United States Patent [19]

Chapman

[11] Patent Number: 5,053,434

[45] Date of Patent: Oct. 1, 1991

[54] DIAMONDOID POLYMERIC COMPOSITIONS

[75] Inventor: Orville L. Chapman, Los Angeles, Calif.

[73] Assignee: Mobil Oil Corporation, Fairfax, Va.

[21] Appl. No.: 598,498

[22] Filed: Oct. 16, 1990

Related U.S. Application Data

[63] Continuation-in-part of Ser. No. 426,609, Oct. 25, 1989, abandoned.

[51] Int. Cl.$^5$ .................. C08J 9/35; C07C 13/28; C07D 241/36
[52] U.S. Cl. .................. 521/52; 585/352; 528/353; 252/312; 252/322
[58] Field of Search .................. 252/174.11; 585/352; 528/353; 521/52

[56] References Cited

U.S. PATENT DOCUMENTS

| | | | |
|---|---|---|---|
| 3,560,578 | 2/1971 | Schneider | 570/187 |
| 4,008,251 | 2/1977 | Moore et al. | 585/352 |
| 4,043,927 | 8/1977 | Duling et al. | 585/352 |
| 4,705,847 | 11/1987 | Hummelen et al. | 585/352 |

OTHER PUBLICATIONS

Bernard F. Hoskins and Richard Robson – Infinite Polymeric Framework Consisting of Three Dimensionally Linked Rod-Like Segments, J. Am. Chem. Soc. 1989, 111, 5962–5964.

Allowed U.S. application 472,530 filed Jan. 30, 1990 to Chapman and Whitehurst.

*Primary Examiner*—John Kight, III
*Assistant Examiner*—John Cooney
*Attorney, Agent, or Firm*—Alexander J. McKillop; Charles J. Speciale; Robert B. Furr, Jr.

[57] ABSTRACT

Polymers are disclosed which comprise monomer units bonded through octahedrally disposed atoms of the monomers. Adamantane exemplifies the skeletal structure of such monomers.

51 Claims, 28 Drawing Sheets

FIG. 5A
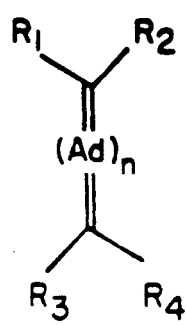
FIG. 5B
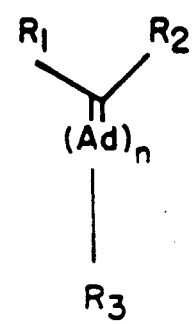
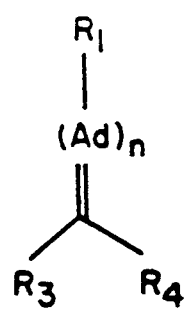
FIG. 5C
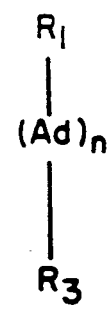
FIG. 5D

FIG. 7A
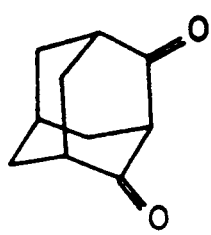
TiCl₃, Na̅ / DIMETHOXYETHANE →
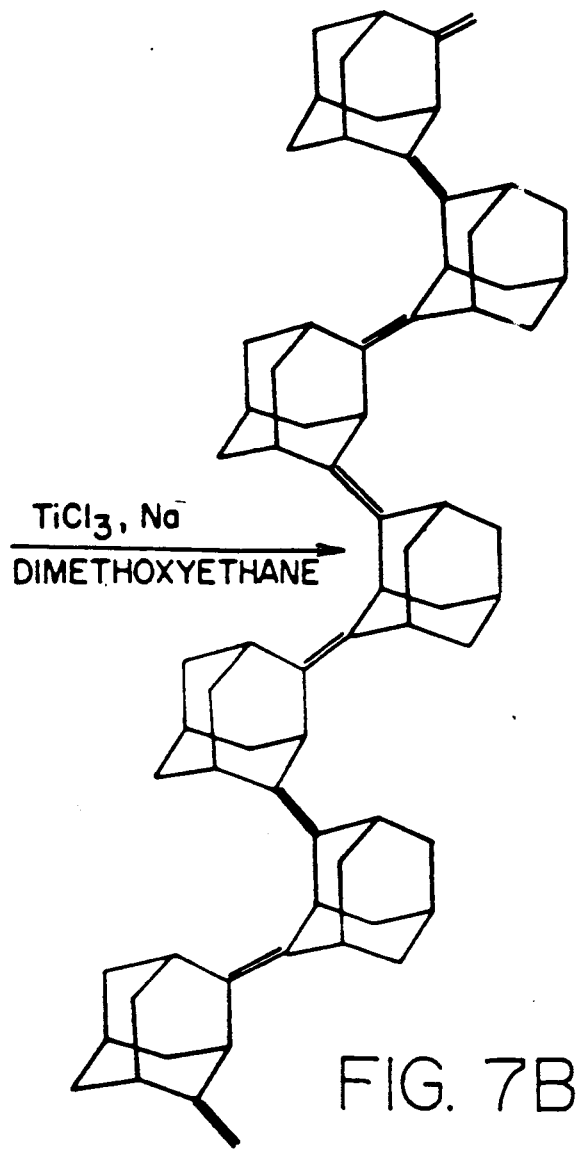
FIG. 7B
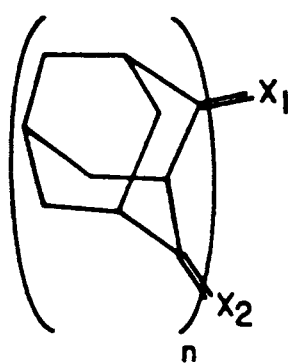
FIG. 7C

DMSO
KHCO$_3$
HEAT

1. NCS
2. DMSO
KHCO$_3$
HEAT

H+

+ ISOMERS

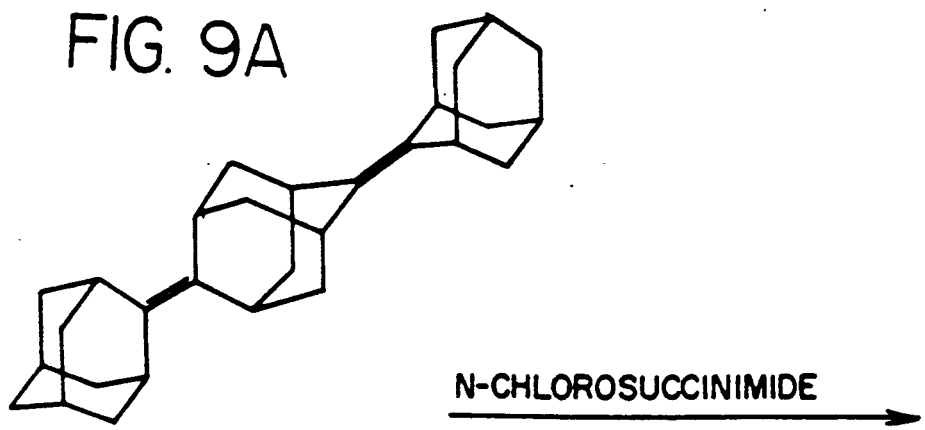
FIG. 9A
N-CHLOROSUCCINIMIDE
FIG. 9B
FIG. 9C
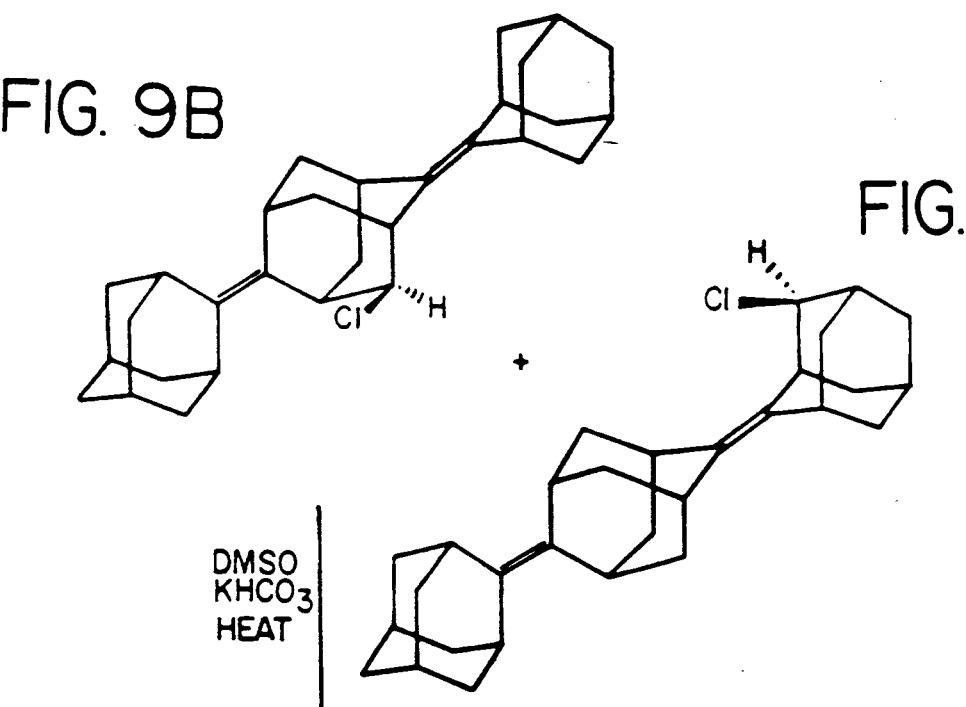
DMSO
KHCO₃
HEAT
FIG. 9D
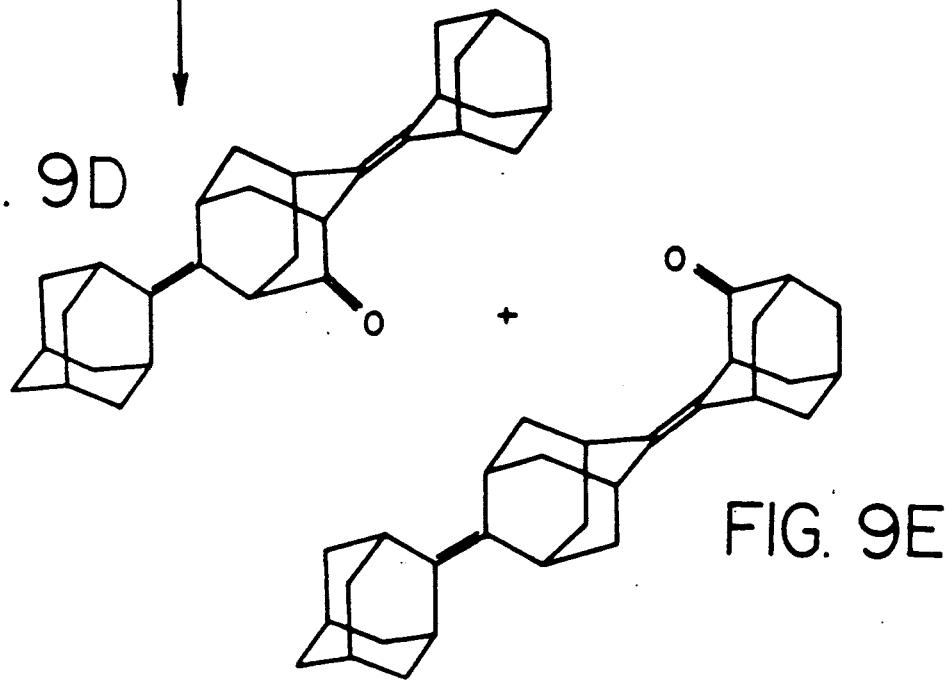
FIG. 9E

+ POLYMER

+ POLYMER

DMSO
KHCO_3
HEAT

1. NCS
2. DMSO
   KHCO_3
   HEAT

FIG. 15A
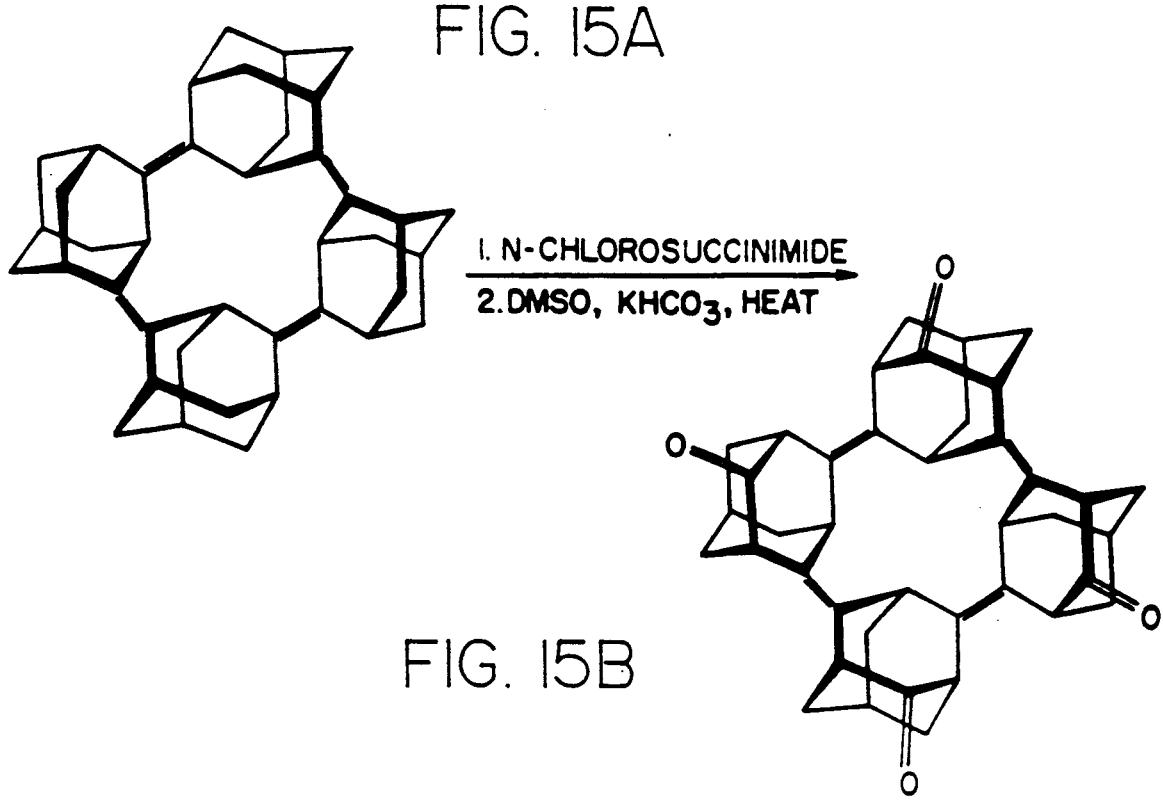
1. N-CHLOROSUCCINIMIDE
2. DMSO, KHCO₃, HEAT
FIG. 15B
McMURRAY REAGENT
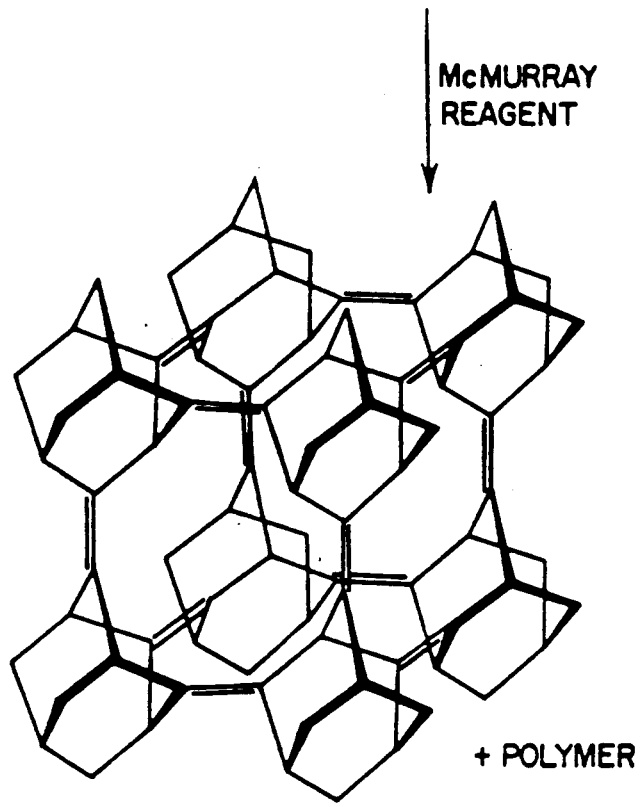
+ POLYMER
FIG. 15C FIG. 18A
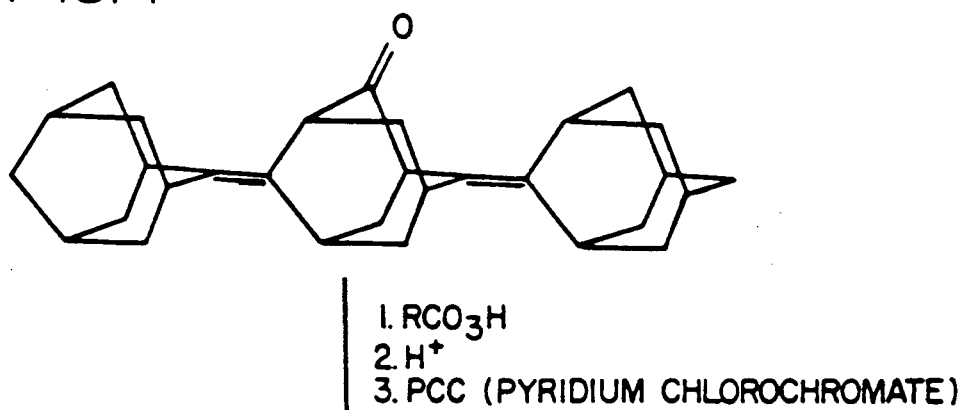
1. RCO$_3$H
2. H$^+$
3. PCC (PYRIDIUM CHLOROCHROMATE)
FIG. 18B
McMURRAY REAGENT
ADAMANTANONE
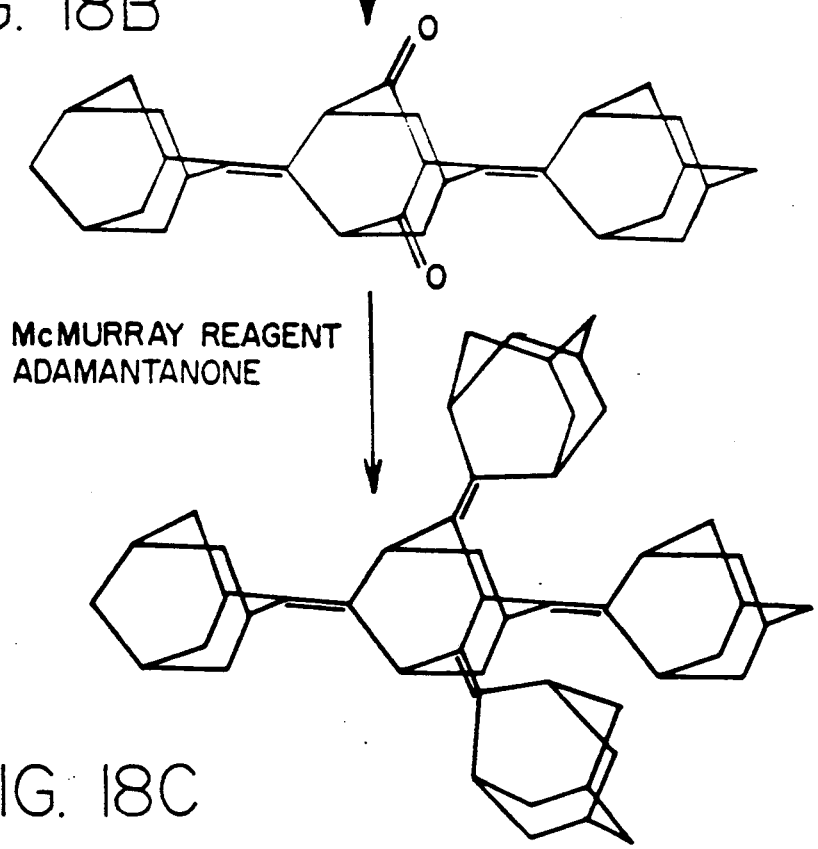
FIG. 18C FIG. 19A
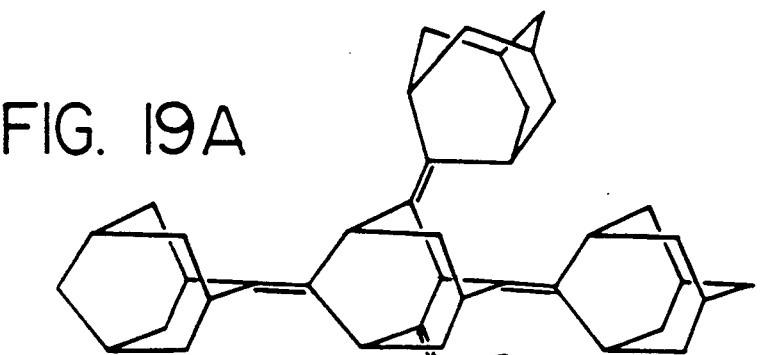
1. NCS
2. DMSO, KHCO₃
3. RCO₃H
4. H⁺
5. PCC
FIG. 19B
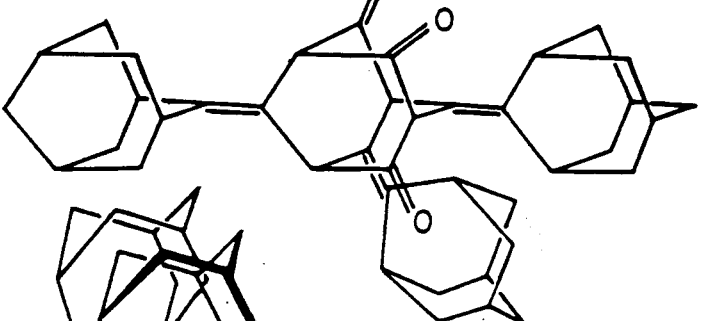
McMURRAY
REAGENT
ADAMANTANONE
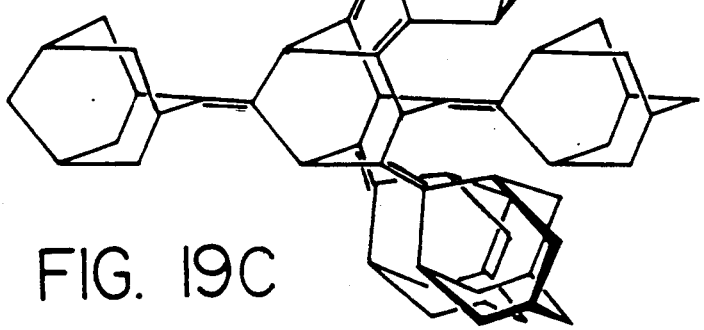
FIG. 19C FIG. 23A
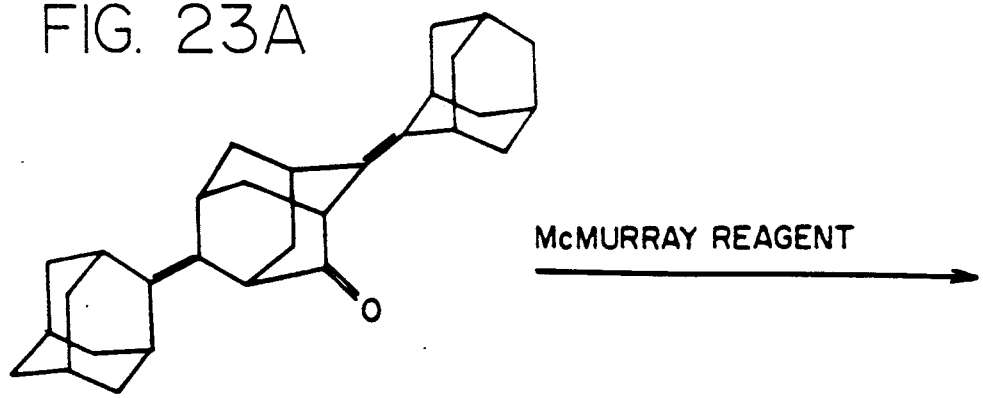
McMURRAY REAGENT →
FIG. 23B
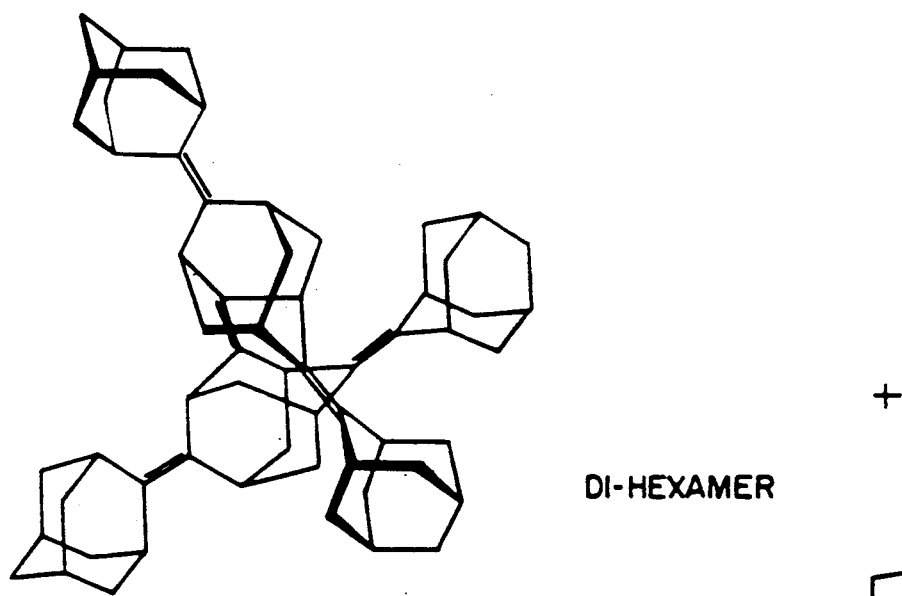
DI-HEXAMER
+
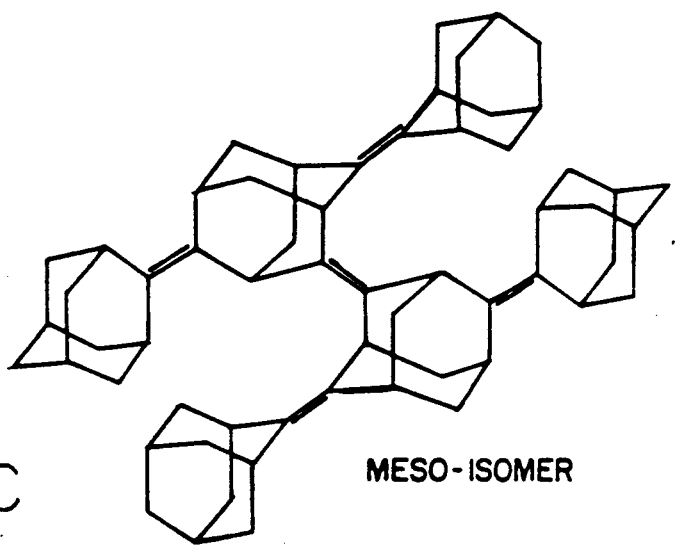
MESO-ISOMER
FIG. 23C

+ POLYMER

1. NCS
2. DMSO
   KHCO₃
   HEAT

+ ISOMERS

FIG. 29A
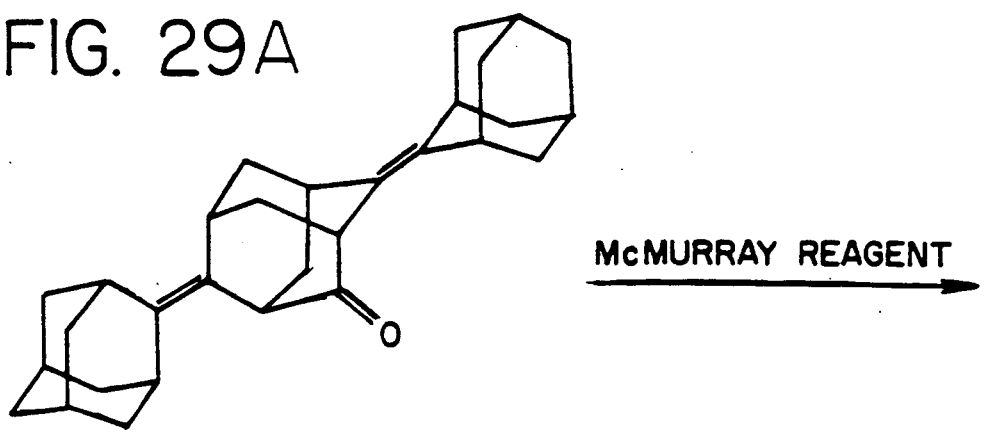
McMURRAY REAGENT →
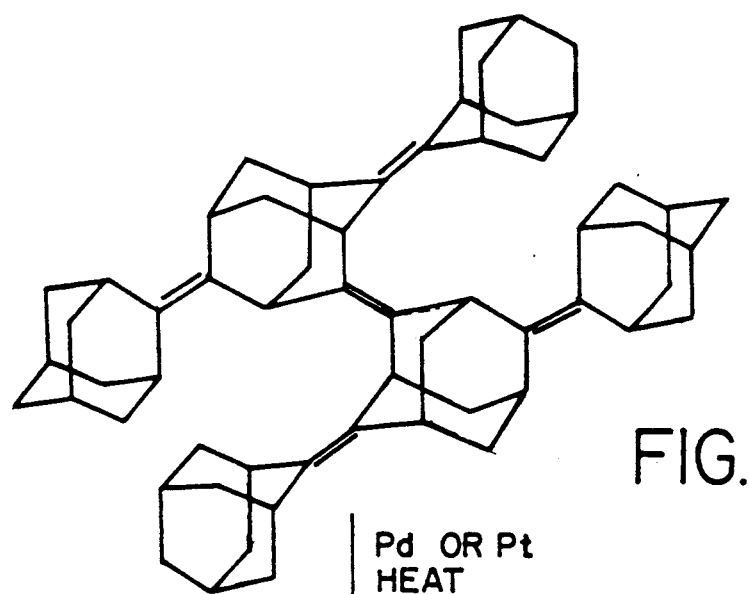
FIG. 29B
Pd OR Pt
HEAT ↓
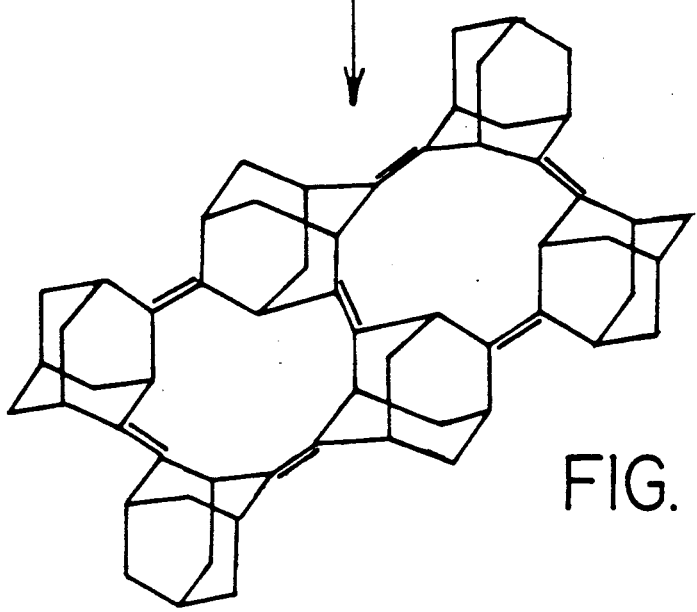
FIG. 29C TiCl₃/Na/THF
OR
TiCl₃/Li/DME → POLYMER

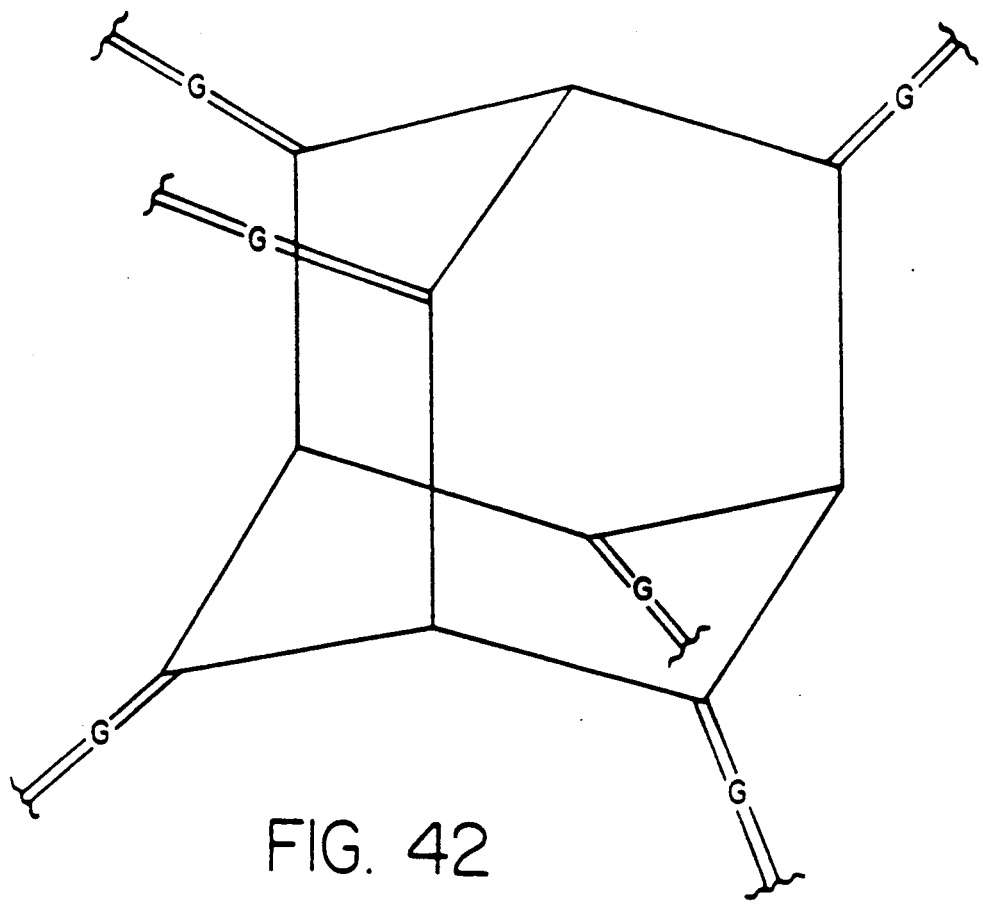
FIG. 42
FIG. 45A FIG. 45B FIG. 45C FIG. 45D FIG. 45E FIG. 45F FIG. 45G
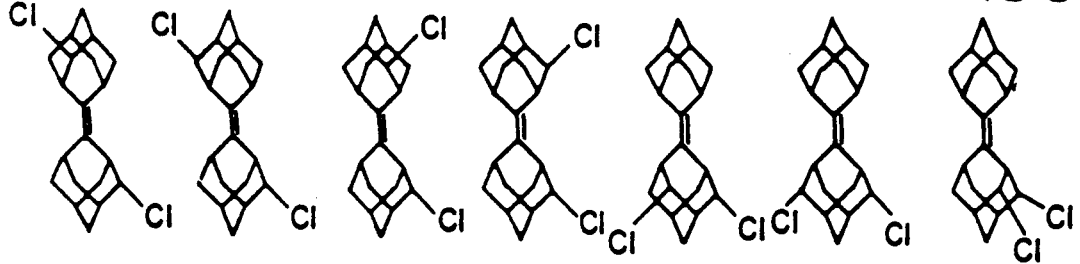
FIG. 46A FIG. 46B FIG. 46C FIG. 46D FIG. 46E FIG. 46F FIG. 46G
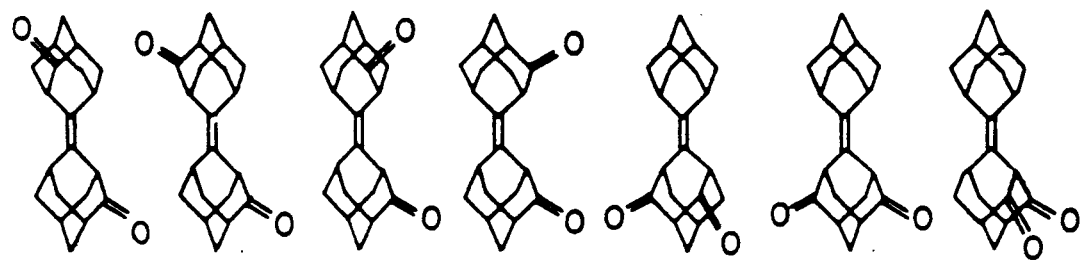

FIG. 43A
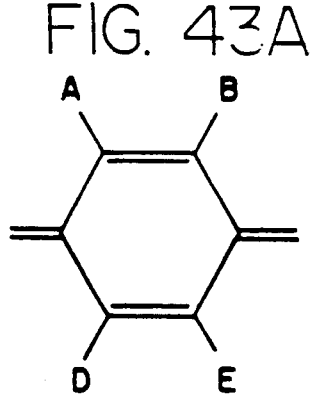
FIG. 43B
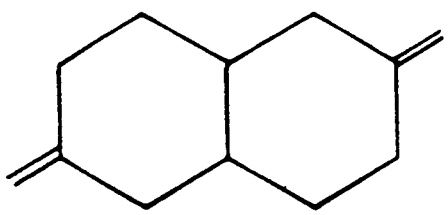
FIG. 43C
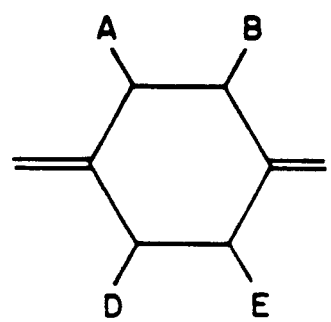
FIG. 43D
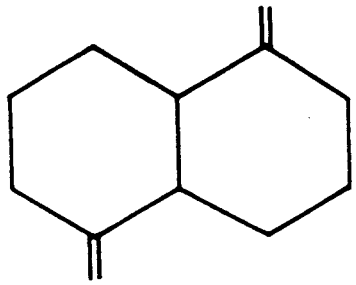
FIG. 43E
FIG. 43F
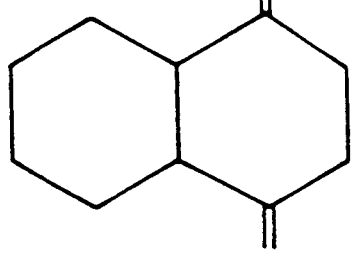
FIG. 43G
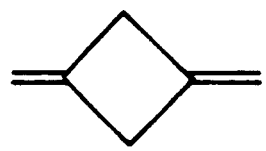
FIG. 43H
$= Ad = (C)_n = Ad =$
FIG. 44A
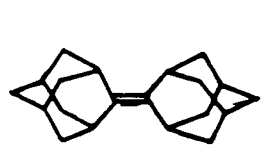 $\xrightarrow{NCS}$
FIG. 44B
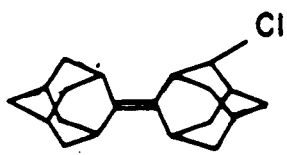 AND/OR DIMER DICHLORIDES

DIAMONDOID POLYMERIC COMPOSITIONS

CROSS-REFERENCE TO RELATED APPLICATIONS

This application is a continuation-in-part of application Ser. No. 426,609, filed Oct. 25, 1989 now abandoned. The entire text of application Ser. No. 426,609 is incorporated herein by reference.

This application is related by subject matter to application Ser. No. 598,499, filed on even date herewith.

FIELD OF THE INVENTION

The present invention relates generally to polymeric compositions of matter comprising monomer units bonded through octahedrally disposed nonmetallic atoms of the monomer.

BACKGROUND OF THE INVENTION

Adamantane, tricyclo-[$3.3.1.1^{3,7}$]decane, is a polycyclic alkane with the structure of three fused cyclohexane rings. The ten carbon atoms which define the framework structure of adamantane are arranged in an essentially strainless manner. Four of these carbon atoms, the bridgehead carbons, are tetrahedrally disposed about the center of the molecule. The other six (methylene carbons) are octahedrally disposed. The illustrations below show the tetrahedral arrangement of the bridgehead carbons and the octahedral arrangement of the methylene carbons.

REFERENCES

The reactivity of the bridgehead and methylene carbons is known. However, the importance of bonding through the octahedrally disposed carbons to form polymers has not previously been recognized. See *Adamantane, The Chemistry of Diamond Molecules*, Raymond C. Fort, Marcel Dekker, New York, 1976. Adamantane has been found to be a useful building block in the synthesis of a broad range of organic compounds, as exemplified by the following references.

U.S. Pat. No. 3,457,318 to Capaldi et al. teaches the preparations of polymers of alkenyl adamantanes useful as coatings, electrical appliance housings, and transformer insulation. The process, yielding polymers bonded through the tetrahedral bridgehead carbons, comprises contacting an adamantyl halide in the presence of a suitable catalyst with a material selected from the group consisting of substituted allyl halides and olefins to produce adamantyl dihaloalkanes or adamantyl haloalkanes as an intermediate product. The intermediate product is then dehalogenated or dehydrohalogenated, respectively, to produce the alkenyl adamantane final product.

U.S. Pat. No. 3,560,578 to Schneider teaches the reaction of adamantane or alkyladamantanes with a $C_3$-$C_4$ alkyl chloride or bromide using $AlCl_3$ or $AlBr_3$ as the catalyst. The reference describes polymerization through $C_3$-$C_4$ linkages connecting bridgehead carbon atoms in the starting adamantane hydrocarbon; See column 3, lines 35-55, as well as the structural illustrations in columns 3-5.

U.S. Pat. No. 3,580,964 to Driscoll discloses polyesters containing hydrocarbyladamantane moieties as well as novel intermediate diesters and crosslinked polymers prepared therefrom. The hydrocarbyladamantane moieties are bonded through the tetrahedral bridgehead carbons; See column 2, lines 6-46 and the diesters illustrated in column 3, lines 55-75.

U.S. Pat. No. 3,639,362 to Dulling et al. discloses novel copolymers having low mold shrinkage properties which are prepared from adamantane acrylate and methacrylates. The adamantane molecule is bonded to the polymer chain through tetrahedral bridgehead carbon atoms.

U.S. Pat. No. 3,649,702 to Pincock et al. discloses a reactive derivative of adamantane, 1,3-dehydroadamantane. The reference shows bridgehead substituents including halogens and alkyls; See column 1, lines 45-64.

U.S. Pat. No. 3,748,359 to Thompson teaches the preparation of an alkyladamantane diamine from an alkyladamantane diacid. The diamine product is illustrated at column 1, lines 20-30, clearly showing bonding through the bridgehead carbons.

U.S. Pat. No. 3,832,332 to Thompson teaches a polyamide polymer prepared from an alkyladamantane diamine. As discussed and illustrated in the Thompson '332 patent at column 2, lines 41-53, the polymer comprises repeating units which include the backbone structure of adamantane. Note that the adamantane structure is bonded to the polymer chain through its bridgehead carbons.

U.S. Pat. No. 3,966,624 to Duling et al. teaches a power transmission fluid containing a saturated adamantane compound. The adamantane compound consists of adamantane-like structures connected through ester linkages, ether linkages, carboxylic acids, hydroxyl or carbonyl groups; See the Abstract as well as column 1, line 49 through column 2, line 50.

U.S. Pat. No. 3,976,665 to Feinstein et al. discloses a dianhydride containing an adamantane group bonded through the bridgehead carbons.

U.S. Pat. No. 4,082,723 to Mayer et al. discloses aza-adamantane compounds for stabilizing polymers to retard degradation by light and heat. The compounds have an adamantane backbone structure with at least one bridgehead carbon replaced by nitrogen. Specified bridgehead carbons may also be replaced by phosphorus, a phosphoryl or thiophosphoryl group, or a methine group optionally substituted by a phenyl or methyl group; See column 1, line 4 through column 2, line 16. While the Mayer et al. patent teaches replacement of a methylene carbon with nitrogen attached to a substituent group, the reference neither teaches nor suggests polymerizing monomers through octahedrally disposed atoms.

U.S. Pat. No. 4,142,036 to Feinstein et al. discloses adamantane compounds having 2 to 4 bridgehead positions substituted with phenylacyl moieties suitable for producing polymers useful for forming shaped objects such as film, fiber, and molded parts. The ester-substituted adamantanes are also suitable as plasticizers for polyvinylchloride and other polymers. The Feinstein et al. '036 patent notes that the four bridgehead carbons are equivalent to each other and are also more susceptible to attack than the secondary carbons. Accordingly, the adamantane component of the polymer taught in Feinstein et al. '036 bonds through the tetrahedrally disposed bridgehead carbons.

U.S. Pat. No. 4,168,260 to Weizer et al. teaches nitrogen-substituted triaza-adamantanyl ureas useful as stabilizers for thermoplastic materials. Nitrogen replaces carbon in three of the four bridgehead positions.

U.S. Pat. No. 4,332,964 to Bellmann et al. discloses diacrylate and dimethacrylate esters containing bridegehead substituted adamantane monomers. The polymer synthesis technique disclosed at column 3, line 62 through column 7, line 61 includes halogen addition at bridgehead carbons followed by replacement of the halogen with the selected link of the polymer chain.

SUMMARY OF THE INVENTION

The present invention encompasses a new class of polymeric compounds which contain at least three monomer units bonded through octahedrally disposed nonmetallic atoms of the monomers. These compounds exhibit unique physical and chemical properties.

Adamantane, a polycyclic alkane having the formula $C_{10}H_{16}$, is one example of a monomer having octahedrally disposed atoms. The structural formula of adamantane is shown in FIG. 1.

Four of the ten carbon atoms are designated $B_1$, $B_2$, $B_3$, and $B_4$. Each of these four carbon atoms is bonded to three other carbons atoms as well as to a single hydrogen. These four carbons atoms will hereinafter be referred to by their common name: the bridgehead carbons. The bridgehead carbons are tetrahedrally disposed with respect to the center of the molecule. This tetrahedral geometry is common in organic chemistry with such elementary examples as the four hydrogens in methane as well as the four methyl groups in 2,2-dimethylpropane. The tetrahedral arrangement of the bridgehead carbons in adamantane is also illustrated in FIG. 1.

The remaining six carbon atoms are each bonded to two (bridegehead) other carbon atoms and to two hydrogen atoms. These non-bridgehead carbons are designated $M_1$, $M_2$, $M_3$, $M_4$, $M_5$, and $M_6$ and will hereinafter be referred to as the methylene carbons. These methylene carbons are octahedrally disposed with respect to the center of the molecule as shown in FIG. 2.

As used herein, the term "octahedrally disposed" refers to points in space which exhibit octahedral geometry with respect to a common center point. The methylene carbons in adamantane define such octahedrally disposed points in space.

The phrases "skeletal structure of adamantane" and "adamantane skeletal structure" as used herein designate a structure comprising four constituents which are tetrahedrally disposed with respect to the center of the molecule and six constituents which are octahedrally disposed with respect to the center of the molecule. Organic compounds exhibiting octahedral geometry are rare. Inorganic compounds commonly exhibit octahedral geometry. There are a few known examples in which organometallic compounds exhibit this arrangement. An example of such an orgamometallic compound is taught by B. F. Hoskins and R. Robson, "Infinite Polymeric Frameworks Consisting of Three-Dimensionally Linked Rodlike Segments", 111 *Journal of the American Chemical Society*, 5962 (1989).

The polymers of the present invention may also include pendant substituent groups replacing one or more hydrogens of the monomer units. These substituent groups may be interposed between monomer units as connecting groups or may be bonded to a monomer unit at the end of a polymer chain, thus forming a terminal substituent group.

As used herein, the term "connecting substituent" refers to a constituent which connects two or more monomers in a polymer. The term "terminal substituent" refers to a constituent other than the repeating monomer unit which ends the polymer chain. The term "pendant substituent" refers to a group attached to the polymer backbone. Terminal substituents are a subset of pendant substituents. Referring to the following structural formula:

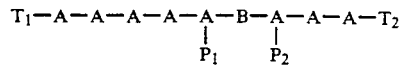

where A is a repeating monomer unit, and B is a connecting substituent which connects two monomers; $T_1$ and $T_2$ are terminal substituents which differ from the repeating monomer and which end the polymer chain; and $P_1$ and $P_2$ are pendant substituents attached to the polymer backbone.

The monomer units comprising the polymers of the present invention may be bonded through one or more of six octahedrally disposed atoms as illustrated above with reference to adamantane. Thus by selecting the number and location of octahedrally disposed atoms through which the monomers are bonded, the resulting polymers may assume linear, zig-zag, laminar, helical, or framework configurations as well as the myriad structures which may be synthesized from combinations of one or more of these configurations.

The skeletal structure of the monomer units themselves may be modified and expanded. The positions occupied by the bridgehead and methylene carbons as illustrated above with reference to adamantane may be occupied not only by atoms other than carbon but also by substituent groups which can be substituted into the skeletal structure. Further, the skeletal structure may be expanded by inserting linear groups of uniform size between each of the bridgehead and each of the adjacent methylene positions. In addition to the inherent functionality of the inserted groups, the inserted groups expand the monomer unit while preserving the octahedral geometry of its bonding atoms.

DESCRIPTION OF THE DRAWINGS

FIG. 5 illustrates additional structures for adamantane rod polymers containing one or more functional groups in the terminal positions, wherein Ad has the skeletal stucture of adamantane and n is at least 3, and preferably is from 5 to 7, and wherein $R_1$ and $R_2$ comprise hydrogen or non-polar (hydrophobic) constituent groups having from 1 to about 20 carbon atoms, and wherein $R_3$ and $R_4$ comprise constituent groups having from 1 to about 20 carbon atoms, with at least one of said $R_3$ and $R_4$ being polar.

FIG. 7 schematically illustrates synthesis of the zig-zag adamantane homopolymer via McMurry coupling of the 2,4-diketone of adamantane. The 2,4-diketone of adamantane is designated 7a and a portion of the resulting zig-zag polymer is designated as 7b. The general structure of the zig-zag adamantane homopolymer is designated 7c.

FIG. 8 further illustrates the acid-catalyzed interconversions between structures 8c and 8f and structures 8d and 8e.

FIG. 9 shows conversion of the linear adamantane trimer, 9a, to the intermediate monochlorinated adamantane trimer, examples of which include 9b and 9c, and subsequently to a mixture of linear adamantane trimer monoketones, two examples of which are designated 9d and 9e.

FIG. 15 shows the conversion of an adamantane cyclic tetramer, 15a, through the cycle tetraketone, 15b, to a mixture of polymers including the framework octamer structure designated as 15c.

FIG. 18 shows conversion of an adamantane trimer monoketone, shown above as structure 9d in FIG. 9, to an intermediate adamantane trimer diketone, 18a, and subsequently to the adamantane pentamer star polymer, 18b, by reaction with adamantane monoketone (adamantanone) in the presence of McMurry reagent.

FIG. 19 shows the conversion of the adamantane pentamer star polymer, designated as 19a, first to the adamantane pentamer star polymer diketone, 19b, and subsequently to the adamantane heptamer star polymer, 19c, via reaction with adamantane monoketone in the presence of McMurry reagent.

FIG. 23 shows synthesis of the meso- and dl-hexamers from the adamantane trimer monoketone designated in FIG. 9 as structure 9a.

FIG. 29 illustrates an alternative synthesis of sheet structures through the adamantane trimer monoketone, 29a. The monoketone 29a is coupled to form the meso-hexamer 29b, which is then converted to the sheet structure 29c at elevated temperature in the presence of a catalyst such as Pd or Pt.

FIG. 37 further shows a suitable synthesis from a triethynladamantane starting material. The triethynladamantane can be synthesized from triacetyladamantane.

FIG. 42 illustrates the inclusion of spacing units G comprising substantially linear groups bonded to one or more moieties in the methylene Z positions.

FIG. 43 shows nonlimiting examples of suitable G substituents for linking adamantane skeletal structures as illustrated in FIG. 42.

FIG. 44 shows the conversion of adamantane dimer, 44a, to the monochlorinated adamantane dimer, one example of which is illustrated as structure 44b.

FIG. 45 shows examples of adamantane dimer dichlorides synthesized in Example XXII.

FIG. 46 shows examples of adamantane dimer diketones derived from the conversion of adamantane dimer dichlorides, examples of which are shown in FIG. 45.

DETAILED DESCRIPTION

The polymers of the present invention comprise at least three monomers bonded through octahedrally disposed non-metallic atoms of the monomers. The monomers may comprise single atoms or molecules at the bridgehead and methylene positions as described above with reference to adamantane. If the monomers include atoms at the bridgehead and methylene positions, these atoms suitably have a valance of 4. Examples of such atoms include the members of Group IVB of the Periodic Table of the Elements, catalog number S-18806, published by Sargent-Welch Scientific Company of Skokie, Ill. 60077. Monomers comprising carbon have been found to exhibit unusual properties as will be described in greater detail hereinbelow.

These polymers may include pendant substituent groups which may be attached to the monomer skeleton connecting substituent groups, interposed between monomer units in the polymer chain, or terminal substituent groups attached to the end of the polymer chain. Nonlimiting examples of such substituent groups include $C_6$-$C_{20}$ aromatics, $C_1$-$C_{20}$ linear and branched alkyl groups, $C_2$-$C_{20}$ linear and branched alkenyl groups, $C_2$-$C_{20}$ linear and branched alkynyl groups, $C_3$-$C_{20}$ cycloalkyl groups, $C_5$-$C_{20}$ cycloakenyl groups, $C_7$-$C_{20}$ cycloalkynyl groups, halogens, amines, diazo compounds, azide compounds, hydrazines, mercaptans, sulfides, polysulfides, ethers, alcohols, esters, organo-metallic compounds, amides, anhydrides, carbamates, ureas, imides, sulfonic acids, sulfinic acids, sulfinates, carboxylic acids, nitriles, isonitriles, heterocycles, metals, phosphates, phosphites, borates, ketones, aldehydes, aryl compounds, acid halides, hydrogen, and the reaction products thereof.

The Linear Adamantane Homopolymer

The linear adamantane homopolymer finds utility in numerous applications including high temperature lubricants, heat transfer fluids and films. The rod-shaped linear adamantane homopolymer is formed via bonding through opposing methylene carbons and is characterized by a substantially square cross-section. This synthesis is described below and in Example XIV and includes the McMurry coupling of 2,6-diketones of adamantane to form the intermediate chain together with McMurry coupling of one adamantane monoketone to each end of the intermediate chain to terminate the polymer.

McMurry coupling of ketones to form symmetrical olefins is taught in U.S. Pat. No. 4,225,734 to McMurry, which is incorporated by reference as if set forth at length herein. See also McMurry, "Improved Procedures for the Reductive Coupling of Carbonyls to Olefins and for the Reduction of Diols to Olefins," 896 *J. Org. Chem.* 41(1976); McMurry et al., "Titanium-Induced Reductive Coupling of Carbonyls to Olefins," 43 *J. Org. Chem.* 3255 (1978); and McMurry, "Titanium-Induced Dicarbonyl-Coupling Reactions", 16 *Acc. Chem. Res.* 405 (1983).

Figure 1:
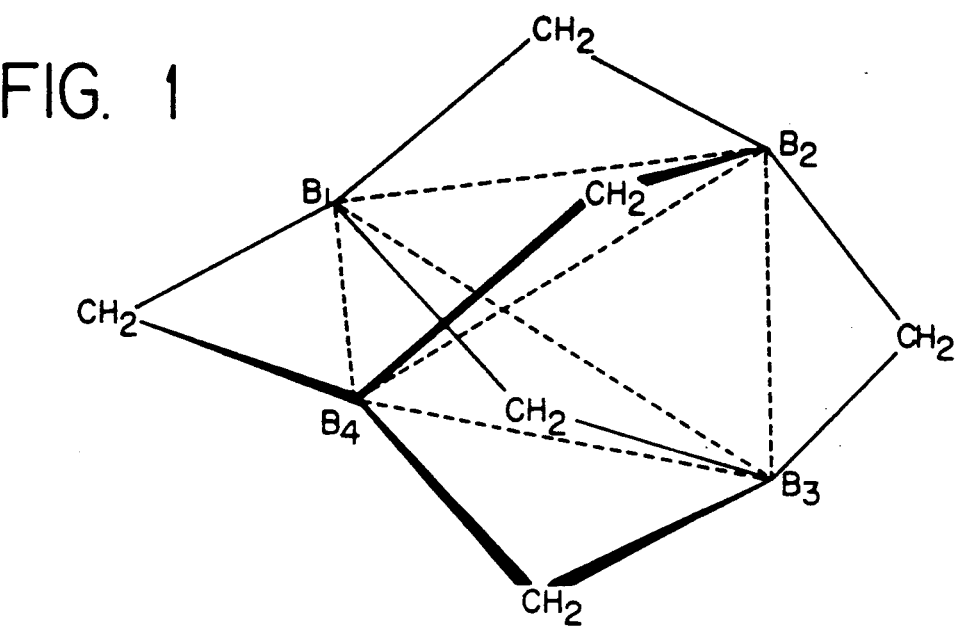
FIG. 1 shows the structural formula of adamantane with the 4 bridgehead carbons designated as $B_1$, $B_2$, $B_3$ and $B_4$.
Figure 2:
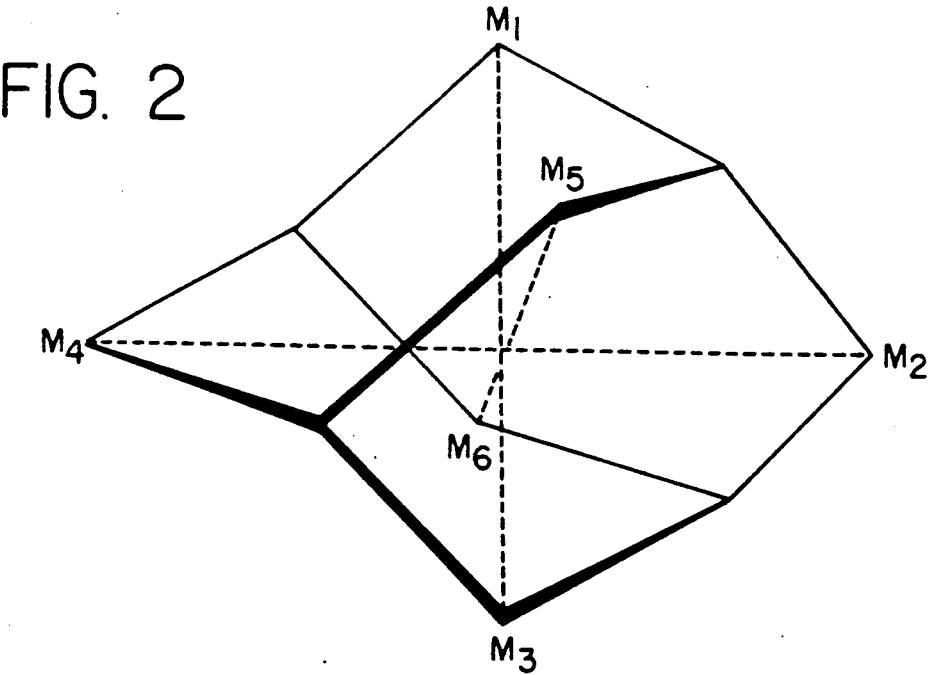
FIG. 2 shows the structural formula of adamantane with the methylene (non-bridgehead) carbons designated as $M_1$, $M_2$, $M_3$, $M_4$, $M_5$ and $M_6$.
Figure 3:
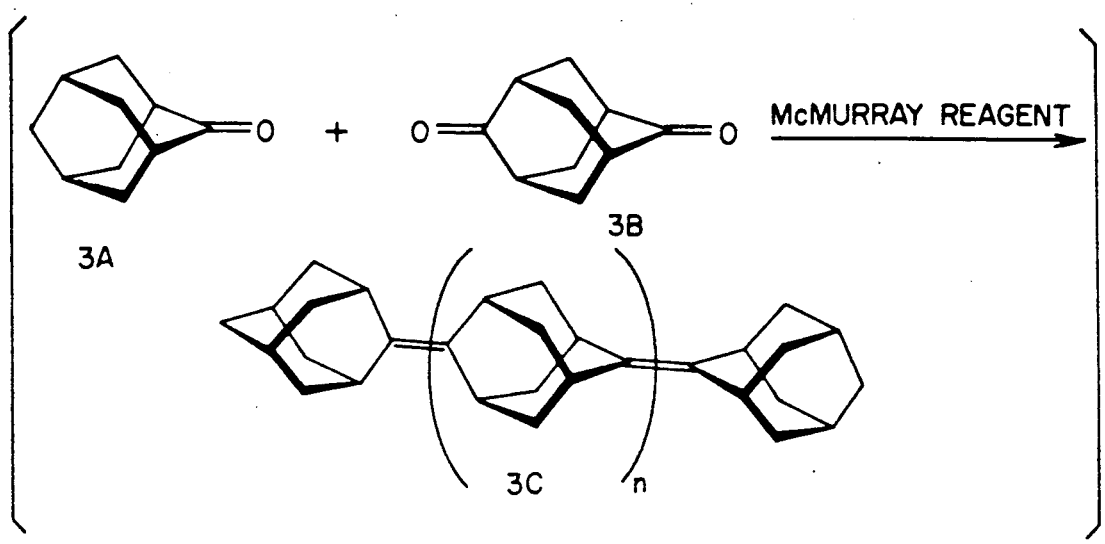
FIG. 3 shows synthesis of the adamantane linear rod polymer via McMurry coupling of at least 2 adamantane monoketone units, 3a, and at least 1 adamantane 2,6-diketone, 3b, to evolve the adamantane linear rod polymer, 3c.

Synthesis of the adamantane linear rod polymer 3c via McMurry coupling is shown in FIG. 3, where n is at least 1 and preferably from 3 to 5000. The adamantane 3a monoketone and diketones 3b may be synthesized from the corresponding chlorinated adamantane as shown below in Example I with reference to the adamantane dimer. The adamantane rod polymer may also be synthesized via olefin metathesis of 2-methylene adamantane and 2,6-dimethylene adamantane in the approximate molar ratio of b 2 mols 2,6-dimethylene adamantane:1 mol 2-methylene adamantane. For a general discussion of olefin metathesis, see Chapters 11 and 14 of K. J. Ivin, *Olefin Metathesis*, Academic Press, New York, 1983, as well as Chapter 4 of V. Dragutan, A. T. Balahan and M. Dimonie, *Olefin Metathesis and Ring Opening Polymerization of Cycloolefins*, John Wiley, New York, 1983, both of which texts are incorporated herein by reference.

An alternative synthesis technique for the adamantane linear rod polymer is described below in Example XVII. The coupling synthesis reacts adamantane monoketones and 2,6-diketones in the presence of $TiCl_3$, Na, and 1,4-dioxane to derive the adamantane linear rod polymer.

Figure 4:
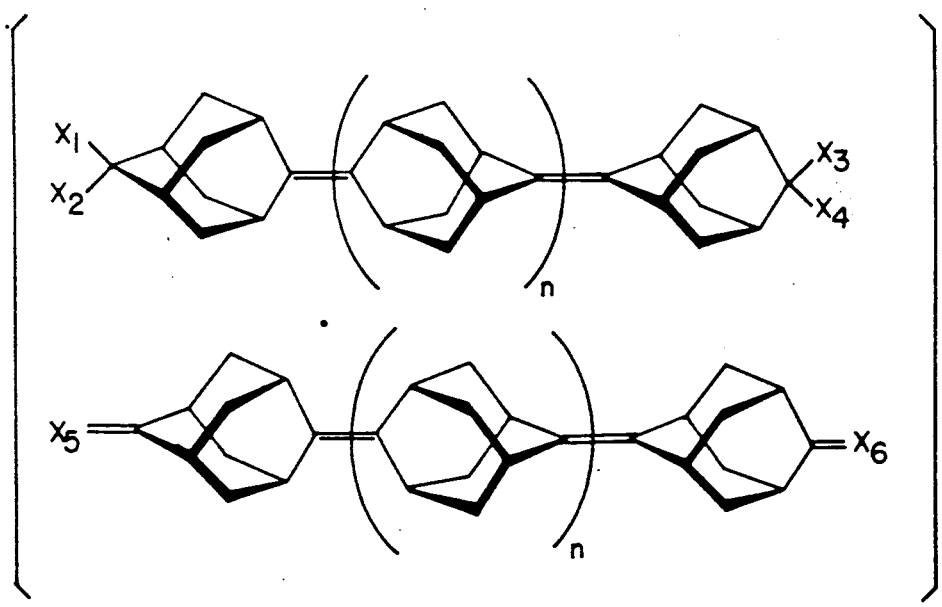
FIG. 4 shows two examples of structures for the linear adamantane rod polymer wherein n is at least 1 and $X_1$ through $X_6$ are substituent groups.

Structures exemplifying the linear adamantane polymer containing terminal substituent groups are shown in FIG. 4, where $X_1$ through $X_6$ are substituents selected from those listed above and n is at least 1, preferably from 3 to 5,000. repeating units.

The linear adamantane homopolymer may further include pendant substituent groups as described above. The terminal monomer groups, i.e. $X_1$ through $X_6$, above, may contain active terminal substituents such as polar groups. The adamantane homopolymer with an added terminal polar group such as carboxylic acid is useful as a barrier film, particularly as a barrier film between a polar liquid, e.g. water, and a nonpolar liquid, e.g. petroleum oil. Such polymers may be suitably synthesized via McMurry coupling of the corresponding ketones, as well as by olefin metathesis. Alternatively, the polymers may be synthesized from the corresponding ketones in the presence of $TiCl_3$, Na, and 1,4-dioxane as described above. The structural formulae designated as 5a, 5b, 5c and 5d in FIG. 5 exemplify such polymers, wherein Ad has the skeletal structure of adamantane and n is at least 3, and preferably is from 5 to 7, and wherein $R_1$ and $R_2$ comprise hydrogen or nonpolar (hydrophobic) constituent groups having from 1 to about 20 carbon atoms, and wherein $R_3$ and $R_4$ comprise constituent groups having from 1 to about 20 carbon atoms, with at least one of said $R_3$ and $R_4$ being polar. The four structures shown above indicate that the terminal substituent groups can be attached either to methylene or bridgehead positions.

Figure 6:
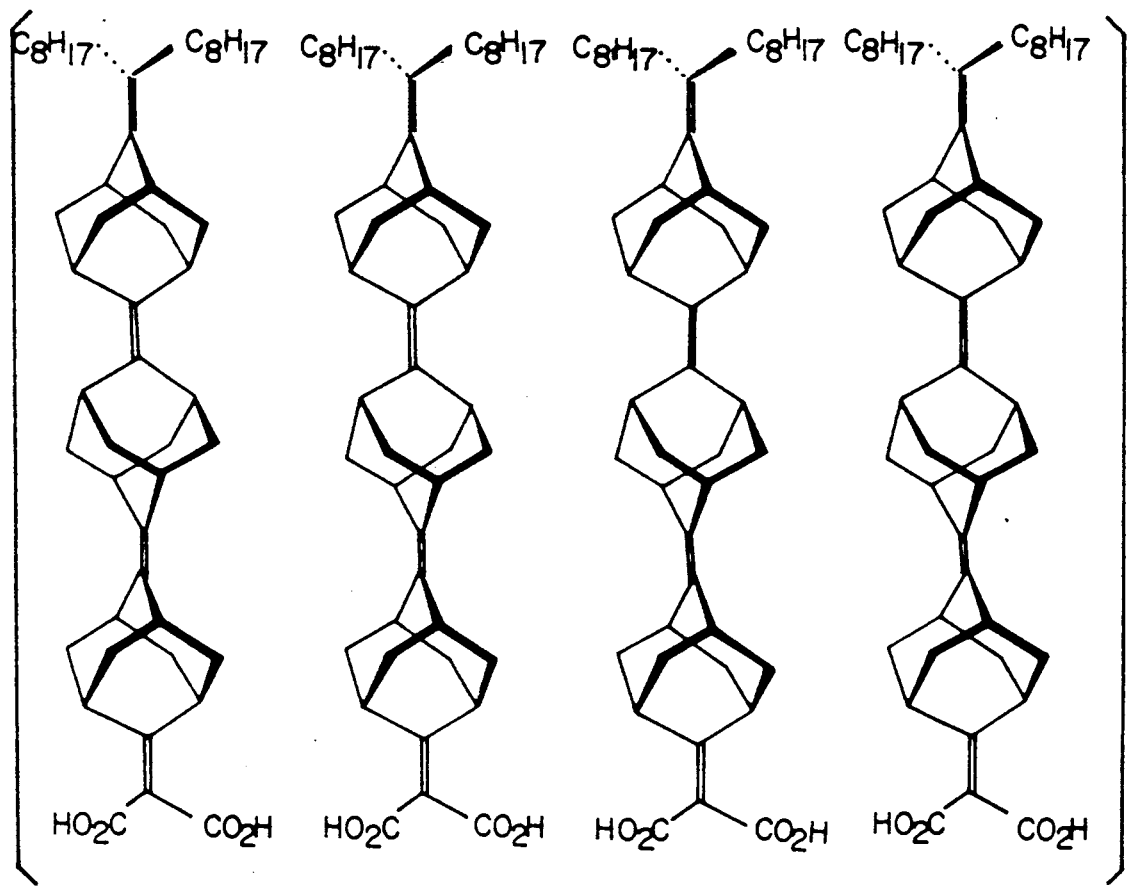
FIG. 6 illustrates four adamantane rod polymers corresponding to the structure 5a of FIG. 5 in which $R_1$ and $R_2$ comprise $C_8H_{17}$, n is 3, and $R_3$ and $R_4$ comprise $CO_2H$.
Figure 8A:
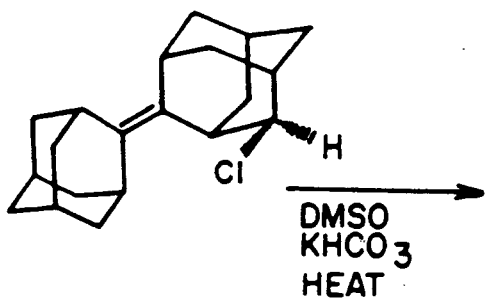
FIG. 8 is a simplified structural illustration showing the synthesis of adamantane dimer diketones from a monochlorinated adamantane dimer. The monochlorinated adamantane dimer starting material is designated as 8a, the intermediate adamantane monoketone dimer is designated as 8b, and four examples of the resulting diketones are designated ad 8c, 8d, 8e and 8f, respectively.
Figure 8B:
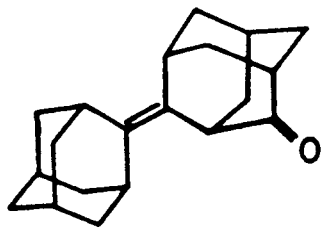
Figure 8C:
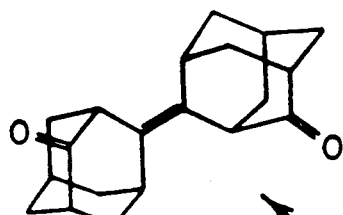
Figure 8D:
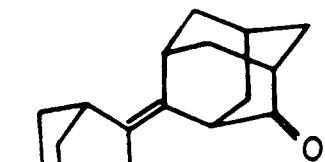
Figure 8E:
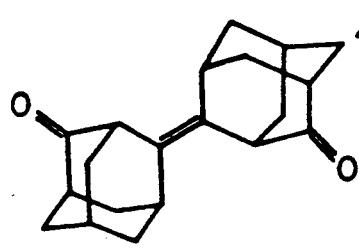
Figure 8F:
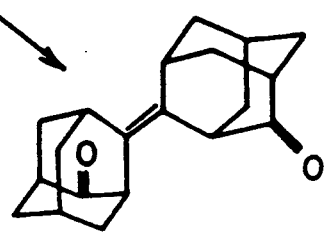

Nonlimiting examples of suitable nonpolar substituents $R_1$ and $R_2$ include normal and branched alkanes, alkene and alkynes, cycloakanes, cycloalkenes and cycloalkynes, as well as aromatics. Nonlimiting examples of suitable polar (hydrophilic) substituents $R_3$ and $R_4$ include ionizable species such as carboxylates, amines, quaternary ammonium salts, sulfonates and phosphates. One example of such a polymer is shown in FIG. 6.

The Zig-Zag Polymer

The zig-zag adamantane homopolymer is formed via bonding through the 2,4-methylene carbons of the adamantane skeleton. Suitable syntheses include the McMurry coupling of 2,4-diketones of adamantane to form the intermediate chain together with McMurry coupling of one adamantane monoketone to each end of the intermediate chain to terminate the polymer. Synthesis of the intermediate chain via McMurry coupling is shown in FIG. 7 with the 2,4-diketone designated as 7a and a portion of the resulting zig-zag structure designated as 7b. An alternate synthesis of the zig-zag polymer is set forth below in Example XXI. The zig-zag polymer may also be synthesized via olefin metathesis of 2,4-dimethyleneadamantane as described above.

The general structure of the zig-zag adamantane homopolymer is shown in FIG. 7 and is designated as 7c, wherein $X_1$ and $X_2$ have the skeletal structure of adamantane, and n is at least 1, preferably 3 to 5,000, more preferably 3 to 500.

The zig-zag polymer may further comprise pendant, terminal and/or connecting substituent groups, illustrative examples of which are listed above.

Potential uses for the zig-zag adamantane homopolymer include high temperature lubricants, heat transfer fluids, and films. The potential uses multiply with the addition of pendant, terminal and/or connecting substituent groups.

Synthesis of Ketone Intermediate Units

The sheet and framework adamantane homopolymers are most preferably synthesized via ketone dimer, trimer and tetramer intermediates.

EXAMPLE I

Synthesis of the Ketone Dimer

The mono-chlorinated adamantane dimer was prepared by the known method of contacting the dimer with N-chlorosuccinimide; see 47 *J. Org. Chem.* 2005 (1982). The adamantane dimer was purchased commercially, but may be synthesized as shown in 38 *Journal of Organic Chemistry* 3061 (1973). The synthesis then proceeds as schematically shown in FIG. 8, with the monochlorinated adamantane dimer designated as 8a, the monoketone adamantane dimer intermediate designated as 8b, and four of the resulting diketones designated as 8c, 8d, 8e and 8f. Further, certain of the resulting structures interconvert in the presence of acid, for example $H_2SO_4$. Specifically, structures 8c and 8d interconvert with structures 8f and 8e as indicated in FIG. 8. Note further that the chlorination of the monochlorinated adamantane dimer designated as 8a yields a complex mixture of products, which mixture contains substantial amounts of compounds other than chloroketones.

EXAMPLE II

Synthesis of the Ketone Trimer

The linear adamantane trimer is prepared as described above via McMurry synthesis. The linear trimer is then converted to the linear monoketone trimer isomers as shown in FIG. 9, by chlorinating the linear trimer 9a to monochlorinated linear adamantane trimers, examples of which include the structures 9b and 9c. The mixture of monochlorinated linear adamantane trimers is then reacted as shown at elevated temperature in the presence of DMSO and $KHCO_3$ to yield a mixture of linear adamantane trimer monoketones, two examples of which are designated 9d and 9e.

EXAMPLE III

Synthesis of the Tetramer

Figure 10:
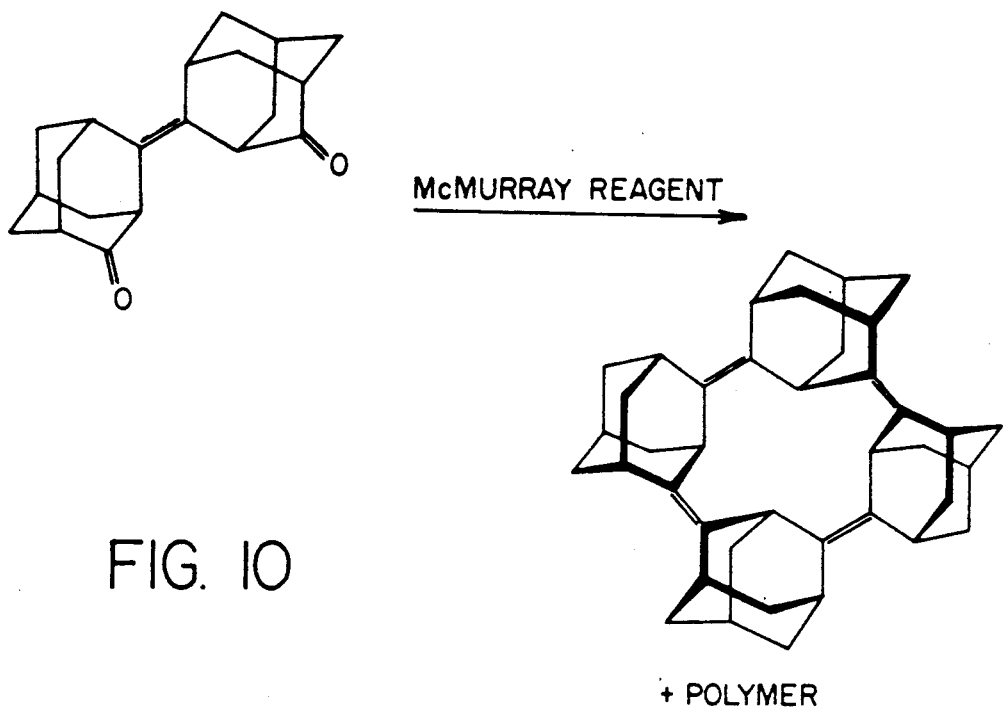
FIG. 10 shows conversion of an adamantane dimer diketone, designated as 8d, above in FIG. 8, to a cyclic adamantane tetramer and polymers.

Diketone 8d of Example I, above, is converted to the cyclic adamantane tetramer in the presence of McMurry reagent as shown in FIG. 10. Alternatively, this diketone dimer may be converted to the cyclic adamantane tetramer in the presence of $TiCl_3/Na/1,4$-dioxane employing the synthesis set forth below in Example XV. The cyclic adamantane tetramer exhibits the sheet structure and is useful as an intermediate building block for framework structures.

EXAMPLE IV

Synthesis of the Ketone Tetramer

Figure 11:
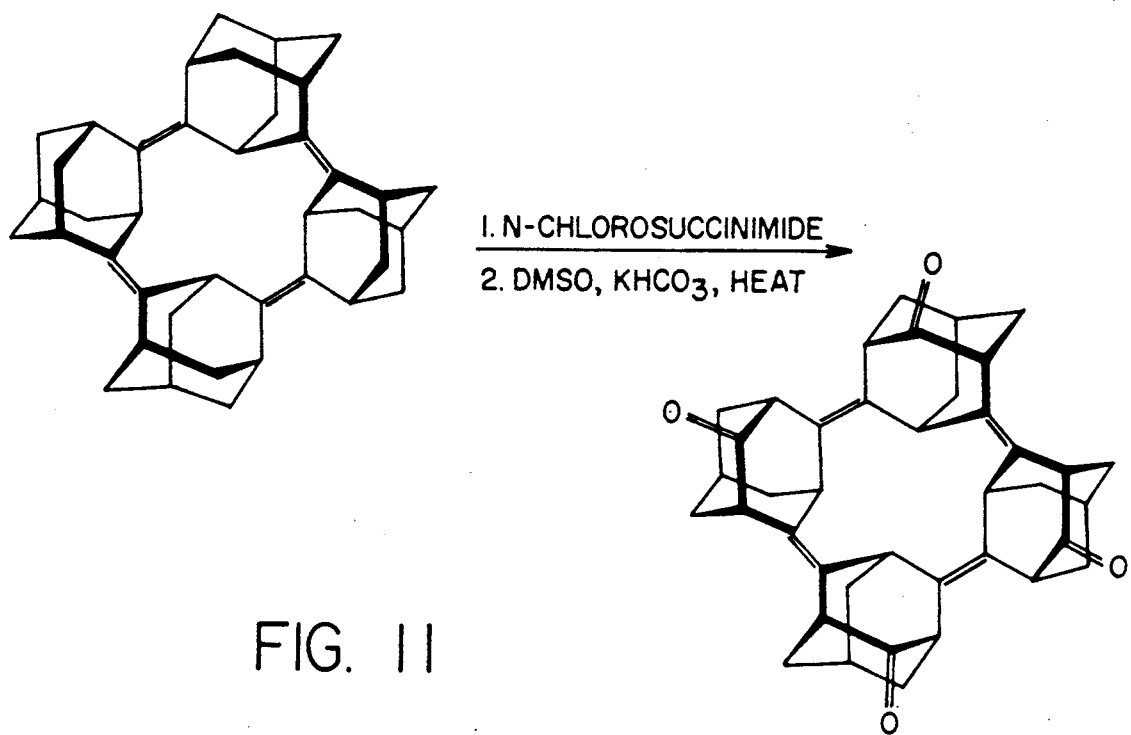
FIG. 11 shows the conversion of the cyclic adamantane tetramer shown in FIG. 10, to the corresponding tetraketone by a two-step synthesis technique.

The cyclic adamantane tetramer of Example III is converted to the tetraketone by the two-step synthesis technique shown in FIG. 11.

The Framework Structure

Figure 12:
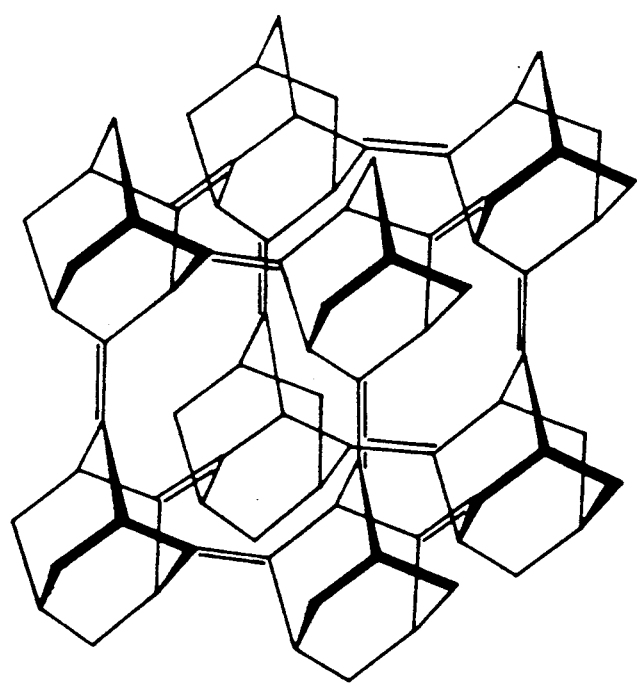
FIG. 12 shows the three-dimensional framework structure formed by 8 adamantane units.
Figure 13A:
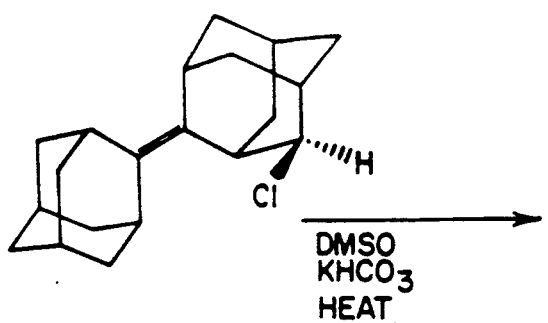
FIG. 13 shows a two-step synthesis of adamantane dimer diketones from a monochlorinated adamantane, 13a, which is converted to the corresponding adamantane dimer monoketone, 13b, and finally to a mixture of adamantane dimer diketones, examples of which are designated 13c, 13d, 13e and 13f. Structures 13c and 13f as well as structures 13d and 13e interconvert in the presence of acid, for example, $H_2SO_4$.
Figure 13B:
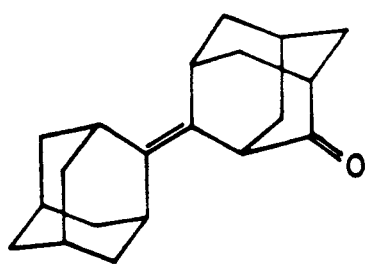
Figure 13C:
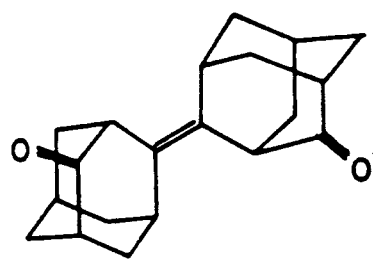
Figure 13D:
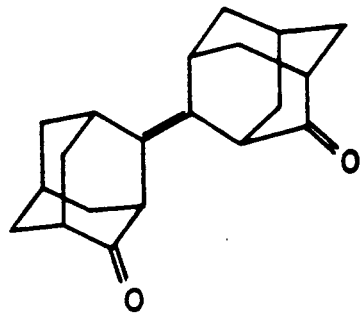
Figure 13E:
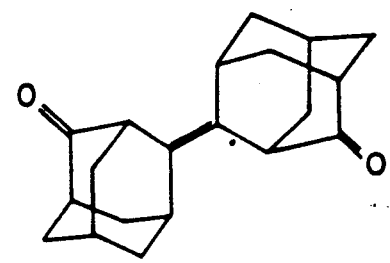
Figure 13F:
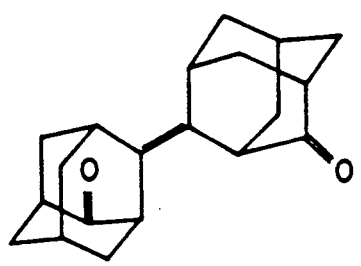
Figure 16A:
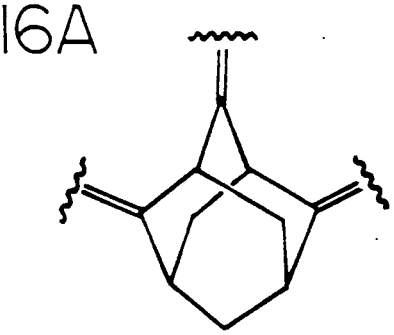
FIG. 16 illustrates four examples of repeating units which can be assembled to form adamantane homopolymer framework structures.
Figure 16B:
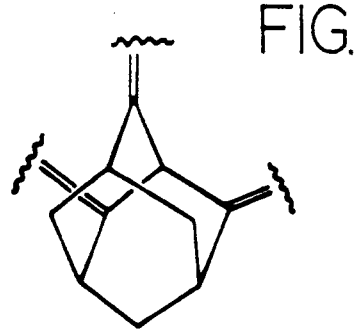
Figure 16C:
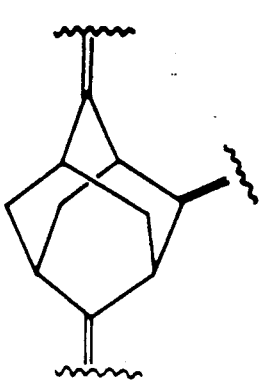
Figure 16D:
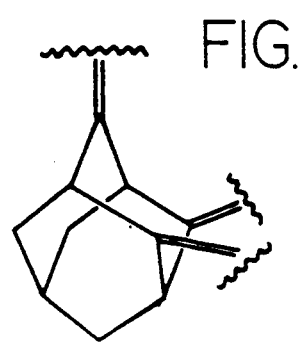
Figure 17A:
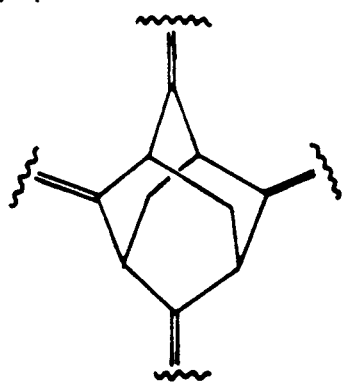
FIG. 17 illustrates four repeating adamantane units which can be assembled to form framework structures.
Figure 17B:
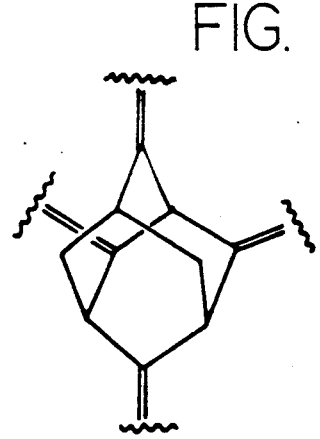
Figure 17C:
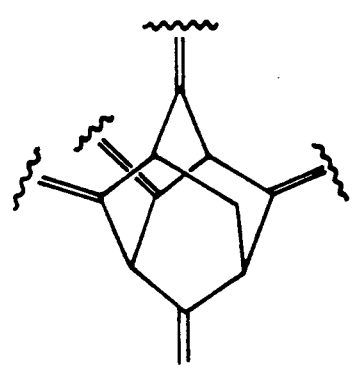
Figure 17D:
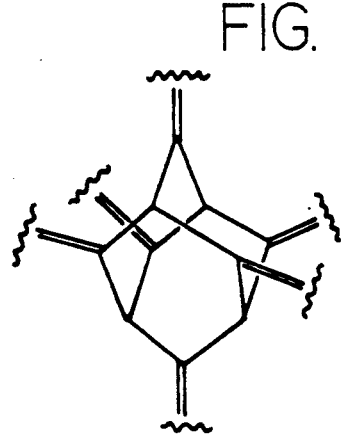

The framework structure formed by polymerizing monomer units through octahedrally disposed nonmetallic atoms of the monomers finds utility as a molecular sieve. The pore openings of the molecular sieve may be adjusted for particular applications by inserting substituent groups between the atoms occupying the bridgehead and methylene positions as described below. The framework structure formed by 8 adamantane units is shown in FIG. 12.

The framework structure is preferably synthesized by first assembling intermediate units such as tetramers and then linking these intermediate units to form the three-dimensional framework structure.

EXAMPLE V

Synthesis of the Framework Structure

Referring to FIG. 13, the monochlorinated adamantane dimer 13a was prepared by reaction with N-chlorosuccinimide as illustrated in Example I. This monochlorinated adamantane dimer was then converted first to the corresponding monoketone 13b, which was then converted to the diketones by the conversion shown in FIG. 13. Examples of the adamantane dimer diketones produced are designated 13c, 13d, 13e and 13f.

Figure 14:
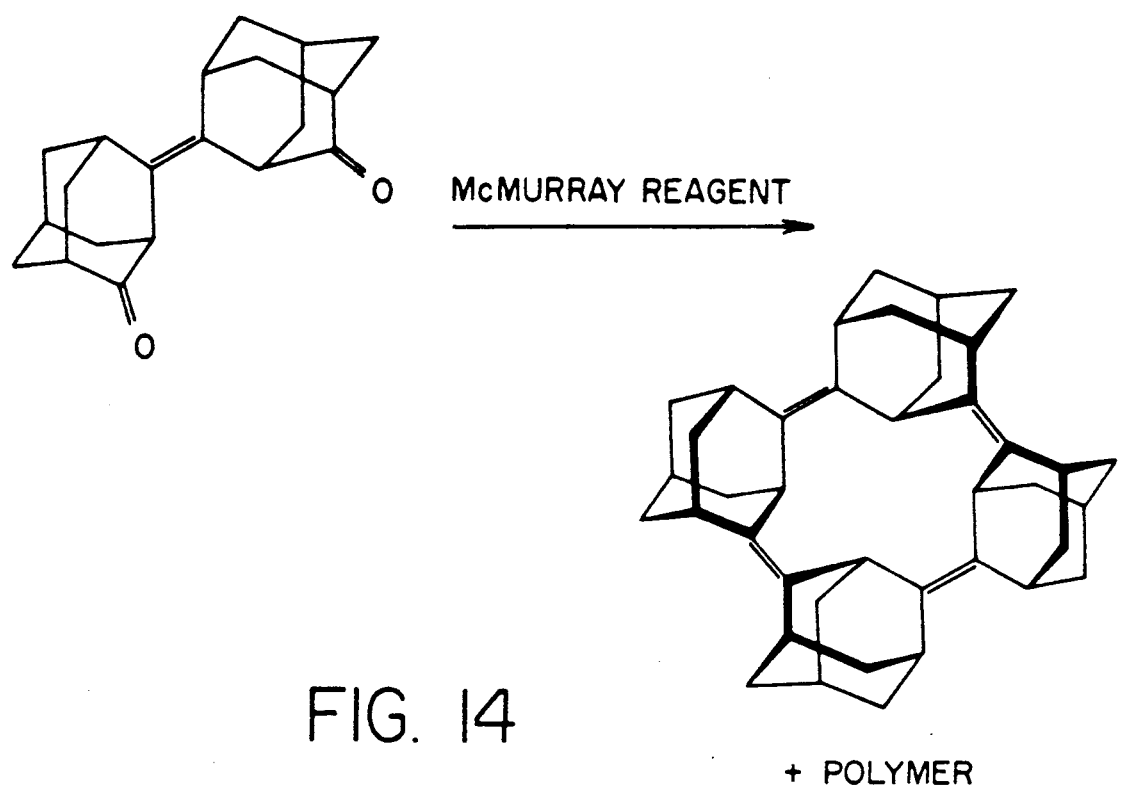
FIG. 14 illustrates one technique for converting adamantane dimer diketone, designated as 13d in FIG. 13, to a cyclic tetramer via McMurry synthesis.

Diketone 13d is isolated and converted to the cyclic tetramer as shown in FIG. 14.

The cyclic adamantane tetramer is then converted to the tetraketone via a two-step process. The tetraketone is then polymerized by McMurry or $TiCl_3/Na/1,4$-dioxane synthesis as shown in FIG. 15.

EXAMPLE VI

Through assemblage of extended sheets, tetramers or octamers, a three-dimensionally extended crystalline network is made. It can be recognized by its characteristic X-ray pattern.

The calculated X-ray diffraction pattern for this adamantane framework polymer is shown in Table I.

TABLE I

| Degrees 2-Theta (CuK α radiation) | Interplanar d-Spacing (A) | $I/I_o$ | |
| --- | --- | --- | --- |
| 15.91 | 5.567 | 13.9 | w |
| 18.39 | 4.821 | 100.0 | vs |
| 26.12 | 3.409 | 0.1 | w |

TABLE I-continued

| Degrees 2-Theta (CuK α radiation) | Interplanar d-Spacing (A) | I/I₀ | |
|---|---|---|---|
| 30.73 | 2.907 | 7.0 | w |
| 32.13 | 2.783 | 16.1 | w |
| 37.27 | 2.411 | 0.1 | w |
| 40.76 | 2.212 | 5.8 | w |
| 41.87 | 2.156 | 0.4 | w |
| 46.08 | 1.968 | 7.8 | w |
| 49.05 | 1.856 | 0.0 | w |
| 53.73 | 1.704 | 1.7 | w |
| 56.41 | 1.630 | 0.1 | w |
| 57.28 | 1.607 | 0.3 | w |

These diffraction data are collected with a diffraction system, using copper K-alpha radiation. The diffraction data are recorded by step-scanning at 0.02 degrees of two-theta, where theta is the Bragg angle. The interplanar spacings, d's, are calculated in Angstrom units (A), and the relative intensities of the lines, $I/I_o$, where $I_o$ is one-hundredth of the intensity of the strongest line, above background, are derived with the use of a profile fitting routine (or second derivative algorithm). The intensities are uncorrected for Lorentz and polarization effects. The relative intensities are given in terms of the symbols vs=very strong (75-100), s=strong (50-74), m=medium (25-49) and w=weak (0-24). It should be understood that diffraction data listed as single lines may consist of multiple overlapping lines which under certain conditions, such as differences in crystallite sizes or very high experimental resolution or crystallographic changes, may appear as resolved or partially resolved lines. Typically, crystallographic changes can include minor changes in unit cell parameters and/or a change in crystal symmetry, without a change in topology of the structure.

The adamantane homopolymer framework structure comprises at least 4 repeating units selected from the group consisting of the four structures illustrated in FIG. 16, and designated as 16a, 16b, 16c and 16d.

Framework structures may also be synthesized which bond through the octahedrally disposed 2,4,6,8,9, and 10-methylene positions. Such framework structures comprise at least 4 repeating units having the structure of the four structures shown in FIG. 17, and designated as 17a, 17b, 17c and 17d.

EXAMPLE VII

Synthesis of Additional Framework Polymers—The Pentamer

Additional framework structures may be synthesized via stepwise addition to the ketone trimer as illustrated below.

To synthesize the adamantane pentamer, the trimer monoketone, structure 9d shown in FIG. 9 and referred to in Example II, is first converted as shown in FIG. 18 to the diketone, 18a. The diketone trimer is then reacted with adamantanone at a molar ratio of about 2 moles adamantanone per mole of diketone trimer in the presence of McMurry Reagent (TiCl₃, Li, dimethoxyethane solvent) or TiCl₃, Na, 1,4-dioxane solvent to form a mixture of polymers including the pentamer star polymer, 18b.

EXAMPLE VIII

Synthesis of Addition Framework Polymers—The Heptamer

The pentamer of Example VII is converted to the heptamer through the pentamer diketone as shown in FIG. 19. Referring now to FIG. 19, the adamantane pentamer star polymer is designated as 19a. NCS represents N-chlorosuccinimide; RCO₃H represents a peroxy acid, for example, perbenzoic, metachloroperbenzoic, or peracetic acid; PCC represents pyridium chlorochromate and DMSO is dimethyl sulfoxide. The adamantane pentamer star polymer 19a is converted as shown to the adamantane pentamer star polymer diketone, 19b. The adamantane pentamer star polymer diketone is then polymerized in the presence of (TiCl₃, Na, dimethoxyethylene) or (TiCl₃, Na, 1,4-dioxane) and about 2 moles of adamantanone per mole of the pentamer diketone to form the adamantane heptamer star polymer shown as 19c.

The adamantane heptamers may then be further polymerized to form framework structures. Suitable synthesis techniques include McMurry synthesis through the ketones as illustrated above.

Figure 20:
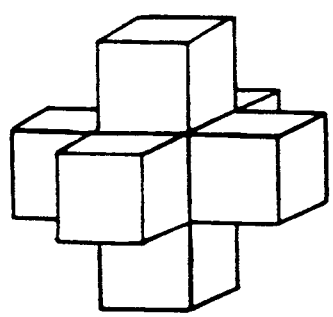
FIG. 20 schematically illustrates the adamantane star heptamer as a three-dimensional Maltese cross in which each adamantane skeletal unit is represented as a cube.
Figure 21:
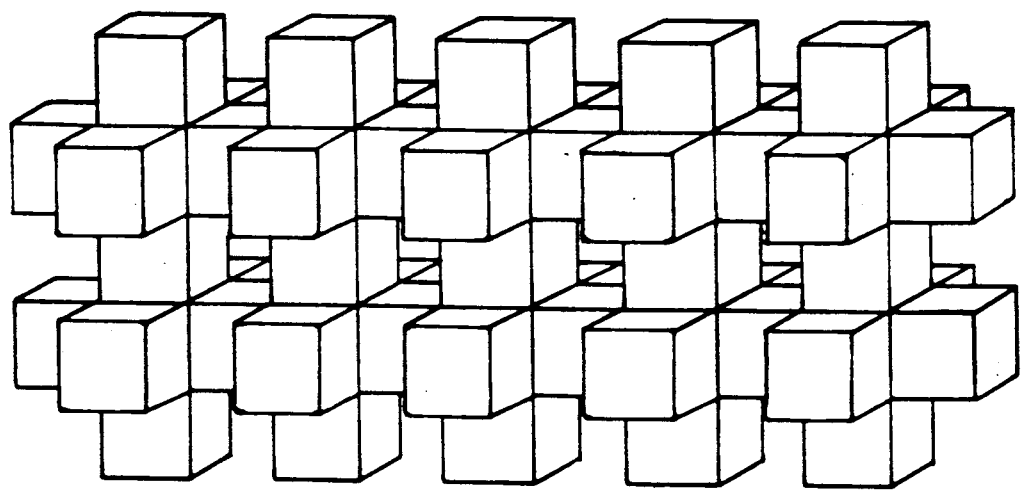
FIG. 21 shows a polymer derived from the heptamers of FIG. 20 by bonding through the octahedrally disposed atoms in the methylene positions of the adamantane skeletal structure.
Figure 22:
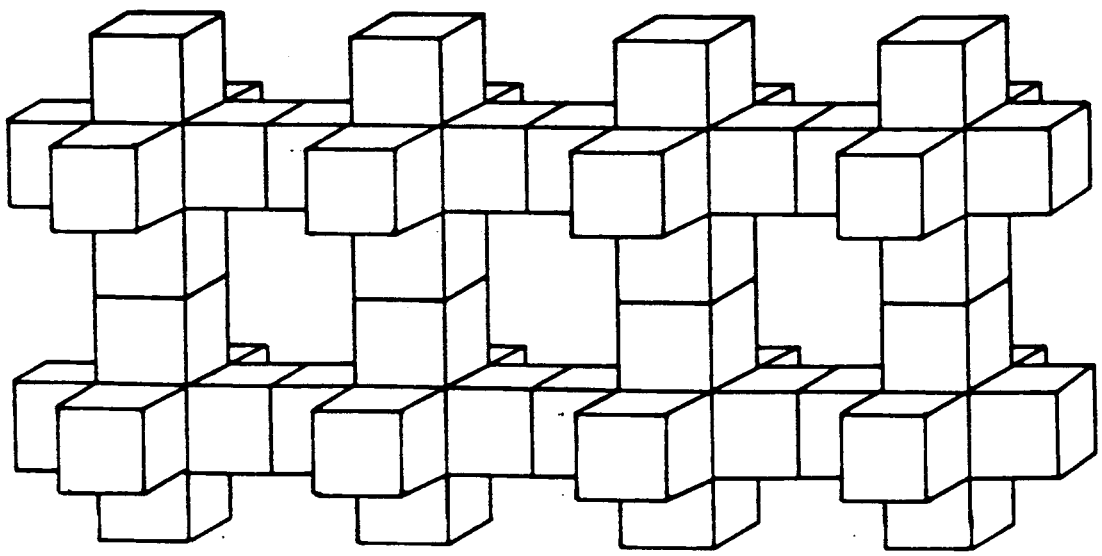
FIG. 22 illustrates a polymer formed from the adamantane star heptamer monomer units of FIG. 20 in which pore sizes are increased by synthesizing a framework structure having a two-unit spacing.

For ease of description, the adamantane heptamer described above in Example VIII can be envisioned as a three-dimensional Maltese cross in which each adamantane skeletal unit can be represented as a cube as shown in FIG. 20. This pictorial description is not rigorously geometrically correct, as the methylene carbons would be located at the center of each of the faces of the cubes. However, this remains an excellent description of polymer assemblage from monomers having the skeletal structure of adamantane. Polymerizing these heptamers by bonding through the octahderally disposed atoms in the methylene position of the adamantane skeletal structure produces a framework structure with regularly spaced pores as shown in FIG. 21. Pore sizes may be increased by synthesizing a framework structure having a unit spacing of 2 or more. A section of such a framework structure having 2 unit spacing is shown in FIG. 22.

EXAMPLE IX

Synthesis of the meso- and dl-Hexamers

Monomer units having the skeletal structure of adamantane may also be assembled to form a dl-hexamer. In Example II, above, the monoketone trimer designated as structure 9a in FIG. 9 may be further polymerized to the meso- or the dl-hexamer. Synthesis of the meso- and dl-hexamers is diagramatically illustrated in FIG. 23, with the dl-isomer designated as 23a and the meso-isomer designated as 23b.

The meso- and dl-Hexamers

The meso-hexamer is a useful intermediate for making small sheet structures comprising one or two cyclic tetramer units. The dl-isomer, on the other hand, exhibits unique stacking characteristics. To visualize such stacking arrangements, the dl-hexamer may be schematically represented by the top view of FIG. 24 in which each of the two rectangles represents an adamantane trimer unit.

Figure 24:
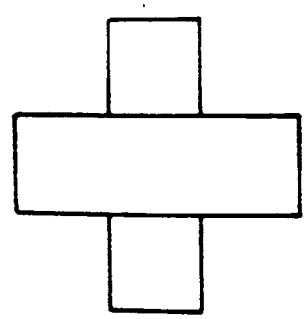
FIG. 24 is a schematic top view of the dl-hexamer.
Figures 25A, 25B:
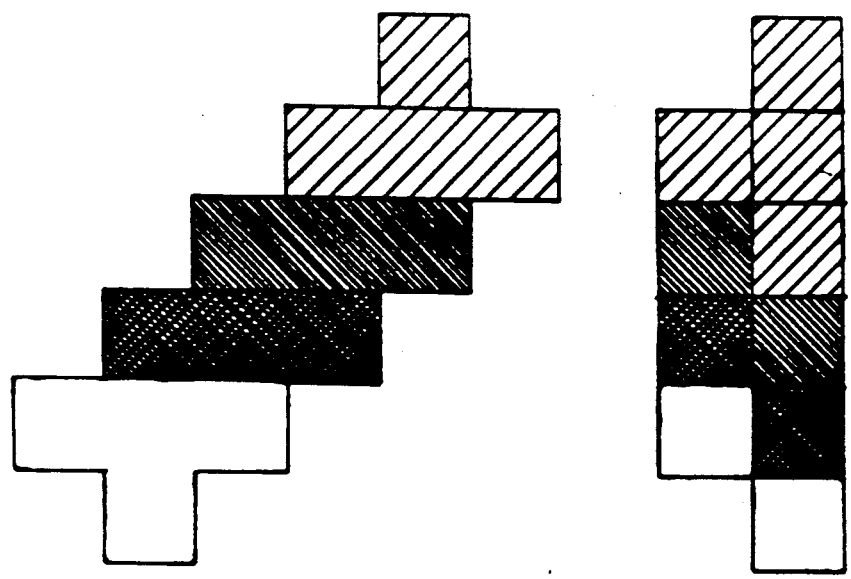
FIG. 25 shows a top view and a side view, designated 25a and 25b, respectively, of packed dl-hexamers of the type shown in FIG. 24.

From the representation of FIG. 24 the packing characteristics of the dl-hexamer may be shown as illustrated in FIG. 25, with the top view designated as 25a and a side view designated as 25b.

Uses for the dl-hexamer and its derivatives include films and lubricant additives.

The Sheet Structure

The sheet structure formed by polymerizing monomer units through octahedrally disposed nonmetallic atoms of the monomers finds utility, among other applications, as a film or coating material. Synthesis of the sheet structure preferably proceeds through intermediates, nonlimiting examples of which include dimers, tetramers, and meso-hexamers.

The sheet structure synthesis through the adamantane dimer is initiated by converting the adamantane dimer to the monoketone of the adamantane dimer. The intermediate is then converted to the diketone and then polymerized via ketone coupling, for example, in the presence of (TiCl$_3$, Na, dimethoxyethane) or (TiCl$_3$, Na, 1,4-dioxane).

EXAMPLE X

Synthesis of the Sheet Structure

Figure 26A:
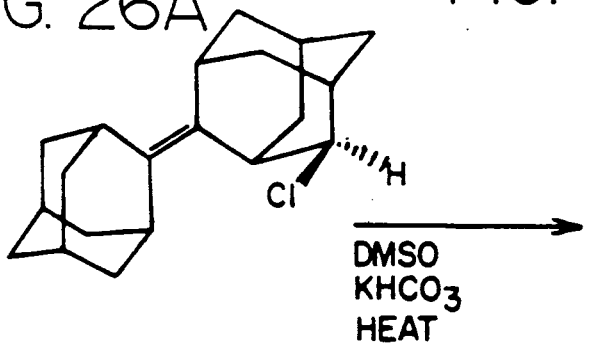
FIG. 26 shows conversion of the monochlorinated adamantane dimer 26a to the corresponding monoketone 26b.
Figure 26B:
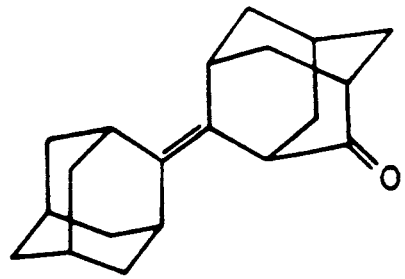

The monochlorinated adamantane dimer shown below was prepared as shown above in Example I. FIG. 26 shows conversion of the monochlorinated adamantane dimer 26a to the monoketone 26b. The monoketone 26b is then converted to a mixture of diketone isomers as shown in FIG. 27 and designated as 27a, 27b, 27c and 27d.

Figure 28A:
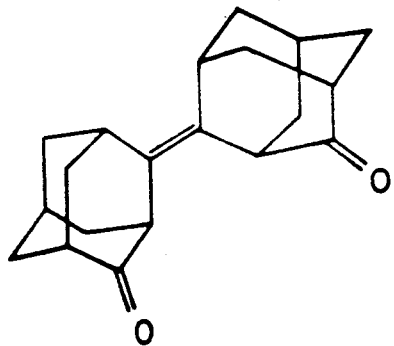
FIG. 28 shows the conversion of diketone 27b, shown in FIG. 27, to the cyclic adamantane tetramer via ketone coupling.
Figure 28A:
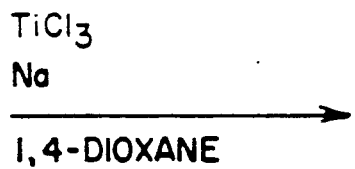
Figure 28B:
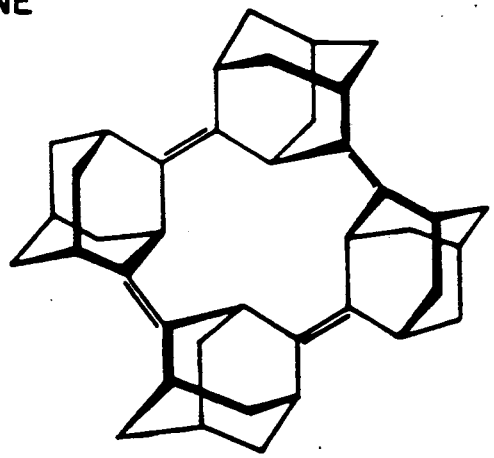
Figure 27A:
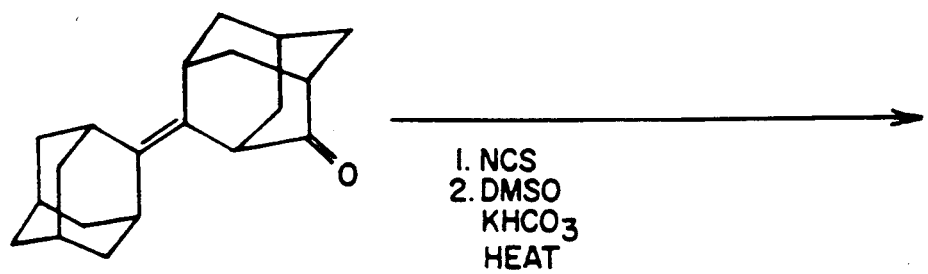
FIG. 27 shows conversion of one of the adamantane dimer monoketones resulting from the synthesis shown in FIG. 26 to a mixture of adamantane dimer diketones, examples of which include the structures 27a, 27b, 27c and 27d.
Figure 27B:
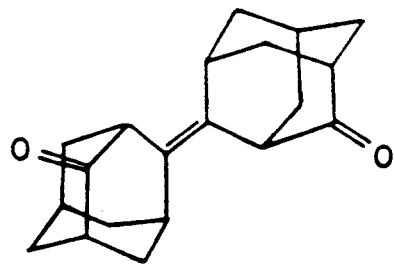
Figure 27C:
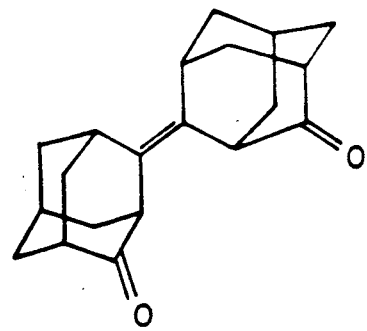
Figure 27D:
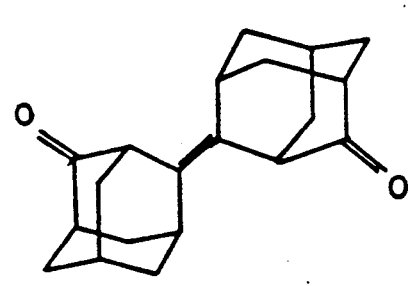
Figure 27E:
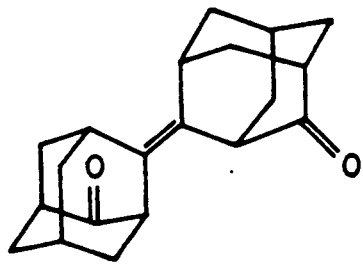

Diketone 27b, shown in FIG. 27, is then converted to the cyclic adamantane tetramer via ketone coupling as shown in FIG. 28. To convert tetramer to larger sheet, sequential synthesis proceeds through the conversion to the di- or tetra-ketone followed by coupling, for example, in the presence of TiCl$_3$, Li, dimethoxyethane (McMurry coupling) or TiCl$_3$, Na, 1,4-dioxane as illustrated in FIG. 28.

EXAMPLE XI

Alternative Synthesis of the sheet Structures

The sheet structure is also synthesized through the mono-ketone, 29a, of the adamantane trimer as schematically illustrated in FIG. 29. The mono-ketone 29a is coupled to form the meso-hexamer, designated as 29b. The meso-hexamer, 29b, is then converted to the sheet structure 29c at elevated temperature in the presence of Pd or Pt.

Figure 30:
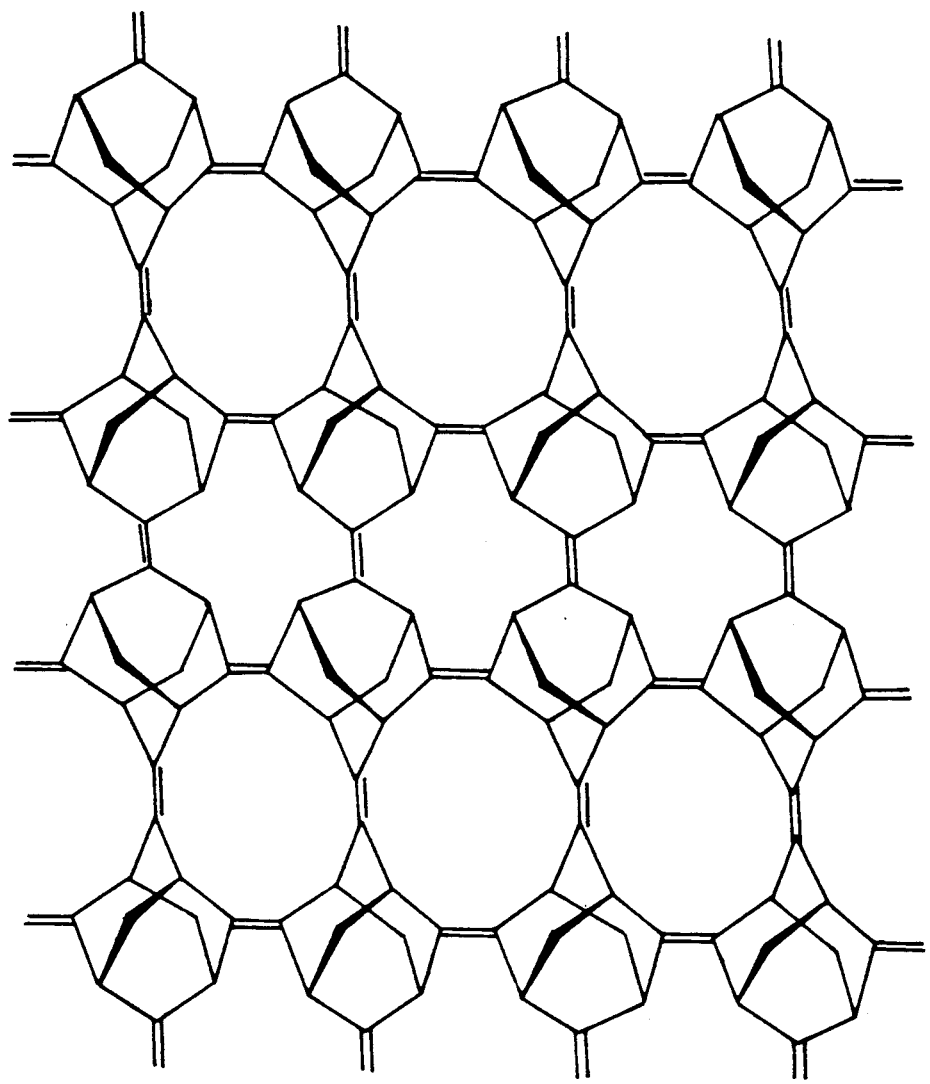
FIG. 30 shows a section of an adamantane-based sheet structure derived from either of the syntheses shown in FIGS. 28 or 29.

A section of an adamantane-based sheet structure derived from this synthesis is schematically illustrated in FIG. 30.

The Helical Structure

The helical structure, forming a rigid or semi-rigid coil spring shape, is useful as an elastomer. The helical polymer may be synthesized via McMurry coupling of the 2,4-diketone as well as through olefin metathesis of the 2,4-dimethyleneadamantane. However, the most preferred synthesis technique for the helical adamantane homopolymer is through diketone 8c, shown in FIG. 8 and described above in Example I.

EXAMPLE XII

Synthesis of the Helical Homopolymer

Figure 31:
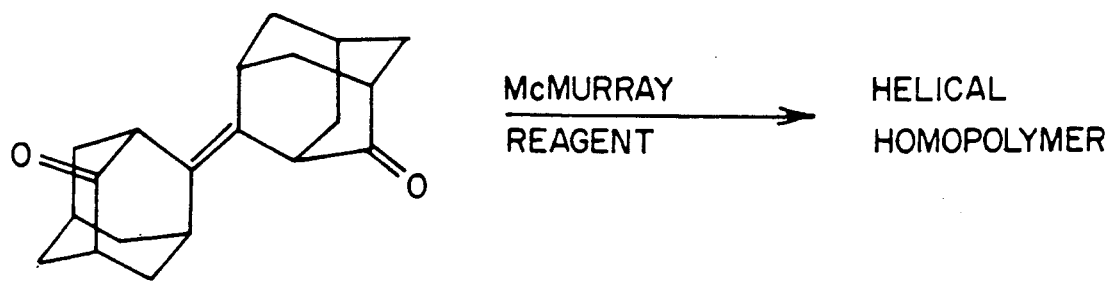
FIG. 31 shows polymerization of an adamantane dimer diketone via McMurry coupling to form the helical adamantane homepolymer.
Figure 32:
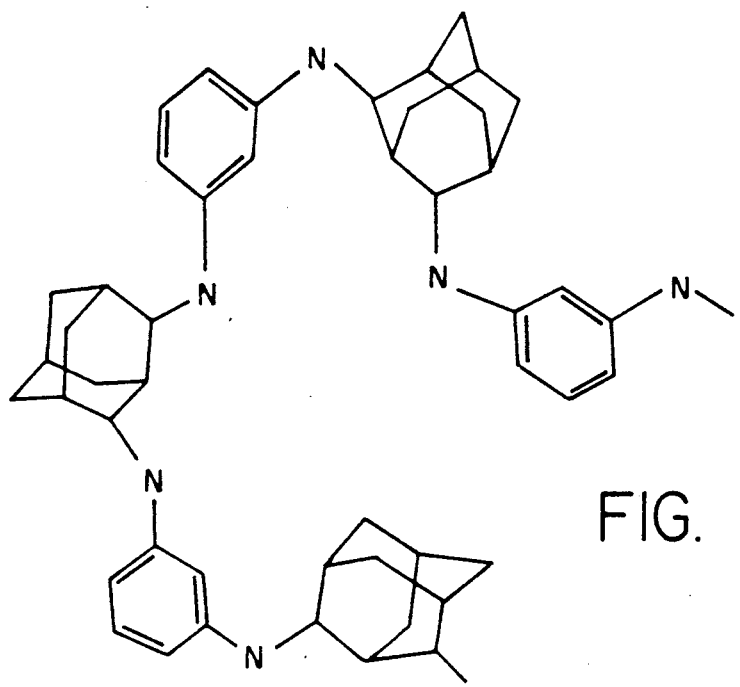
FIG. 32 illustrates a helical adamantane polymer in which adamantane is copolymerized with a second monomer unit, specifically 2,4-diketoadamantane, 2,6-diketoadamantane and 1,3-diaminobenzene and 1,4-diaminobenzene are copolymerized to produce a mixed helical polymer, a section of which is shown.

The diketone dimer shown in FIG. 31 is polymerized via McMurry coupling to form the helical adamantane homopolymer. The monomer unit having octahedrally disposed atoms may also be copolymerized with a second monomer unit, as is exemplified by the combination of 2,4- and 2,6-diketoadamantane with 1,3- and 1,4-diaminobenzene. A section of the resulting polymer is schematically illustrated in FIG. 32. The helical polymer typically comprises from 5 to 5,000 repeating units bonded through octahedrally disposed nonmetallic atoms of the repeating units.

The Expanded Adamantane Skeleton

The skeletal structure of the monomer units themselves may be modified and expanded. The positions occupied by the bridgehead and methylene carbons as illustrated above with reference to adamantane may be occupied not only by atoms other than carbon but also by substituent groups which can be substituted into the skeletal structure through tetrahedrally located bonds of the substituent groups. Further, the skeletal structure may be expanded by inserting rigid semi-rigid linear groups of uniform size between each of the atoms or substituent groups occupying the bridgehead methylene positions. In addition to the contributing properties inherent to the functionality of the rigid linear groups, these inserted groups expand the monomer units while preserving its octahedral geometry. The expanded and-/or substituted adamantane skeleton may then be used in its monomeric form as a thermally stable fluid or may be polymerized as described above through its octahedrally disposed nonmetallic atoms.

Figure 33:
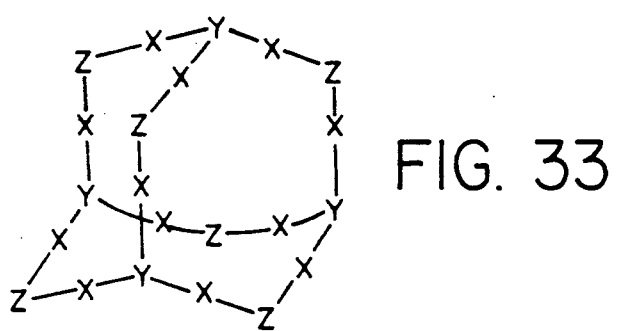
FIG. 33 shows a substituted and/or expanded adamantane skeletal structure.

The substituted and/or expanded adamantane skeleton is shown in FIG. 33.

Figure 34:
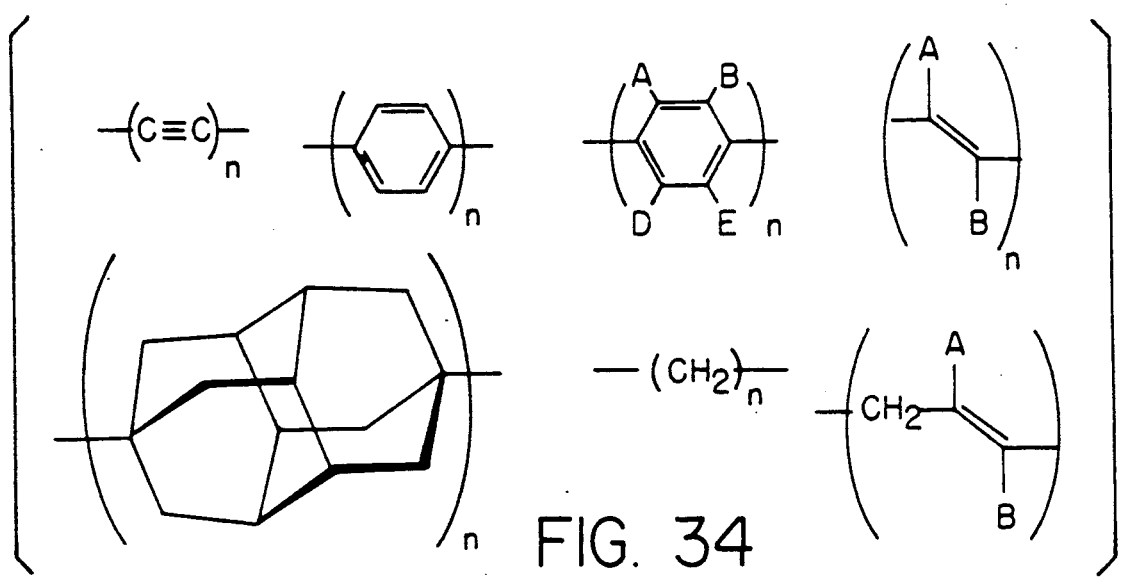
FIG. 34 shows nonlimiting examples of suitable substituents for the skeleton-expanding X positions shown in FIG. 33.

Nonlimiting examples of suitable substituents for the skeleton-expanding X positions include approximately linear substituents such as the examples shown in FIG. 34, where A, B, D AND E are substituents including C$_6$–C$_{20}$ aromatics, C$_1$–C$_{20}$ alkyl groups, C$_2$–C$_{20}$ alkenyl groups, C$_2$–C$_{20}$ alkynyl groups, halogens, amines, diazo compounds, azide compounds, hydrazines, mercaptans, sulfides, polysulfides, ethers, alcohols, esters, organometallic compounds, amides, anhydrides, carbamates, ureas, imides, sulfonic acids, sulfinic acids, sulfinates, carboxylic acids, nitriles, isonitriles, heterocycles, metals, phosphates, phosphites, borates, ketones, aldehydes, aryl compounds, acid halides, hydrogen, and the reaction products thereof; and n is at least 1.

Figure 35:
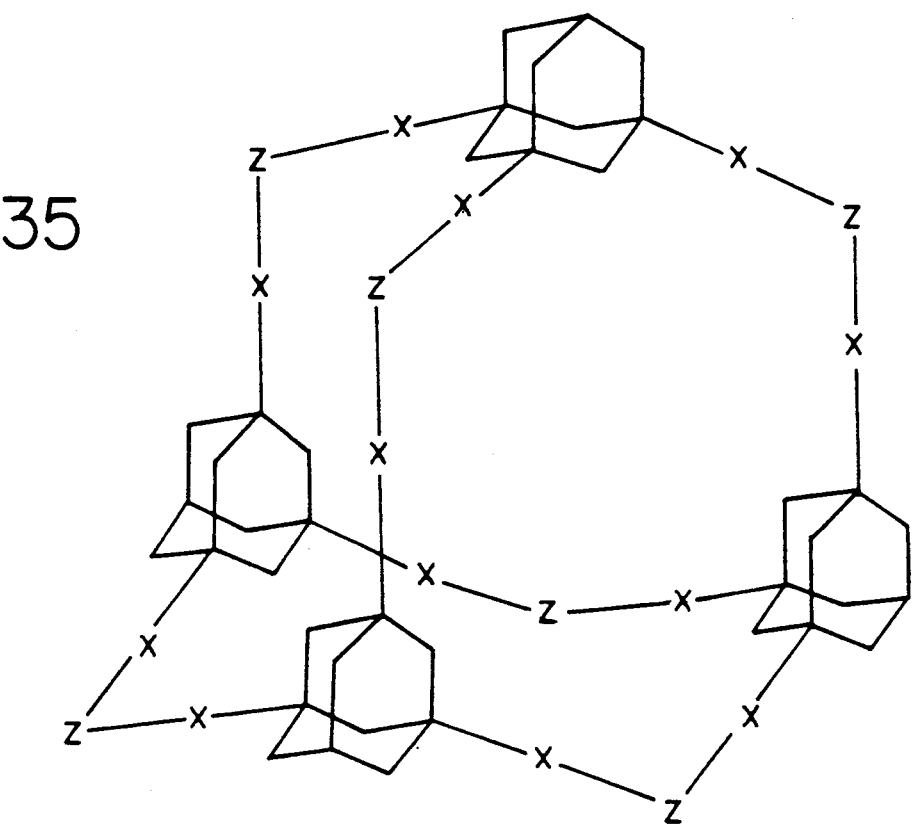
FIG. 35 shows an expanded adamantane skeleton in which the Y positions are replaced with adamantane.

Nonlimiting examples of suitable substituents of the bridgehead Y positions include tetrahedral substituents such as the elements of Group IVB of the Periodic Table of the Elements. Molecules exhibiting tetrahedral bonding arrangements are also useful as Y position substituents. For example, the tetrahedral disposition of the bridgehead positions in an adamantane-like skeleton as shown in FIG. 33 may be used to substitute such adamantane-like skeletal structures into the bridgehead and methylene positions of a larger adamantane-like structure. These structures may then be used alone or as monomers to polymerize through the octahedrally disposed methylene positions as described above. An example of Y replacement with adamantane is shown in FIG. 35.

Nonlimiting examples of suitable substituents for the methylene Z positions include tetrahedral substituents as described with reference to the bridgehead positions.

The following nonlimiting examples of X, Y, and Z replacements are provided as illustrations of such substitutions.

X Replacement

Figure 36:
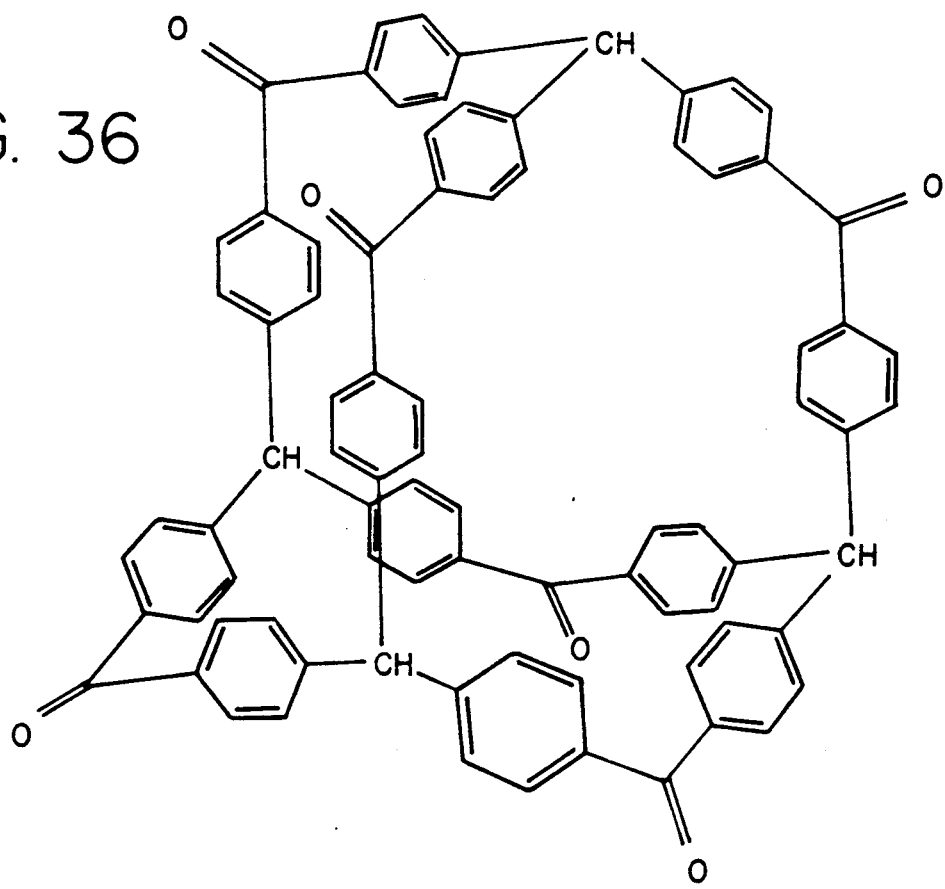
FIG. 36 illustrates an expanded admantane skeleton in which a benzene ring is interposed between each of the bridgehead and methylene positions.

Interposing a benzene ring between each of the bridgehead and methylene positions in the ketone-substituted adamantane skeleton yields the structure shown in FIG. 36.

EXAMPLE XIII*

X and Y Replacement

Figure 37:
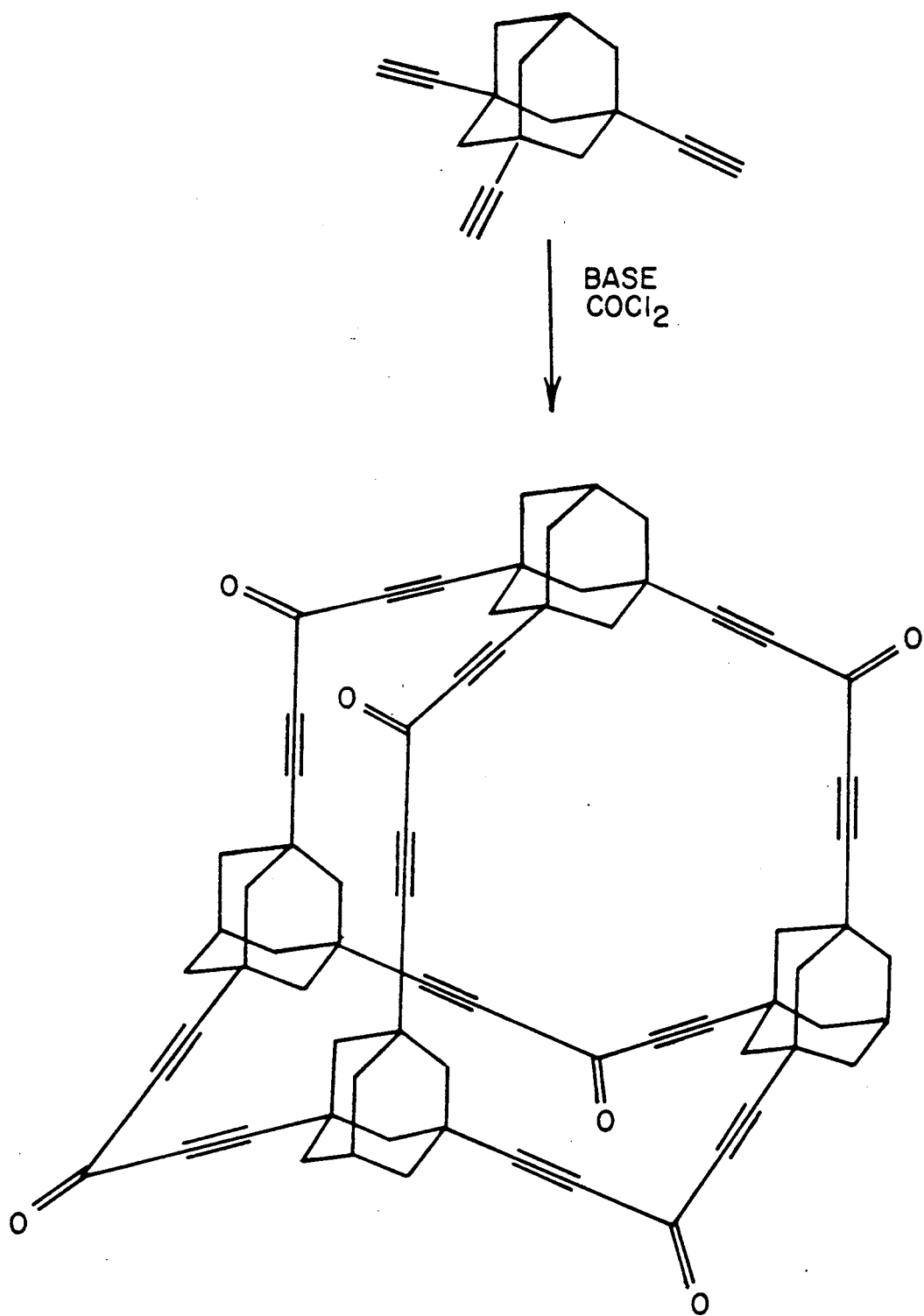
FIG. 37 illustrates one example of X and Y replacement in which acetylene is in the X position and adamantane is in the Y position.
Figure 38:
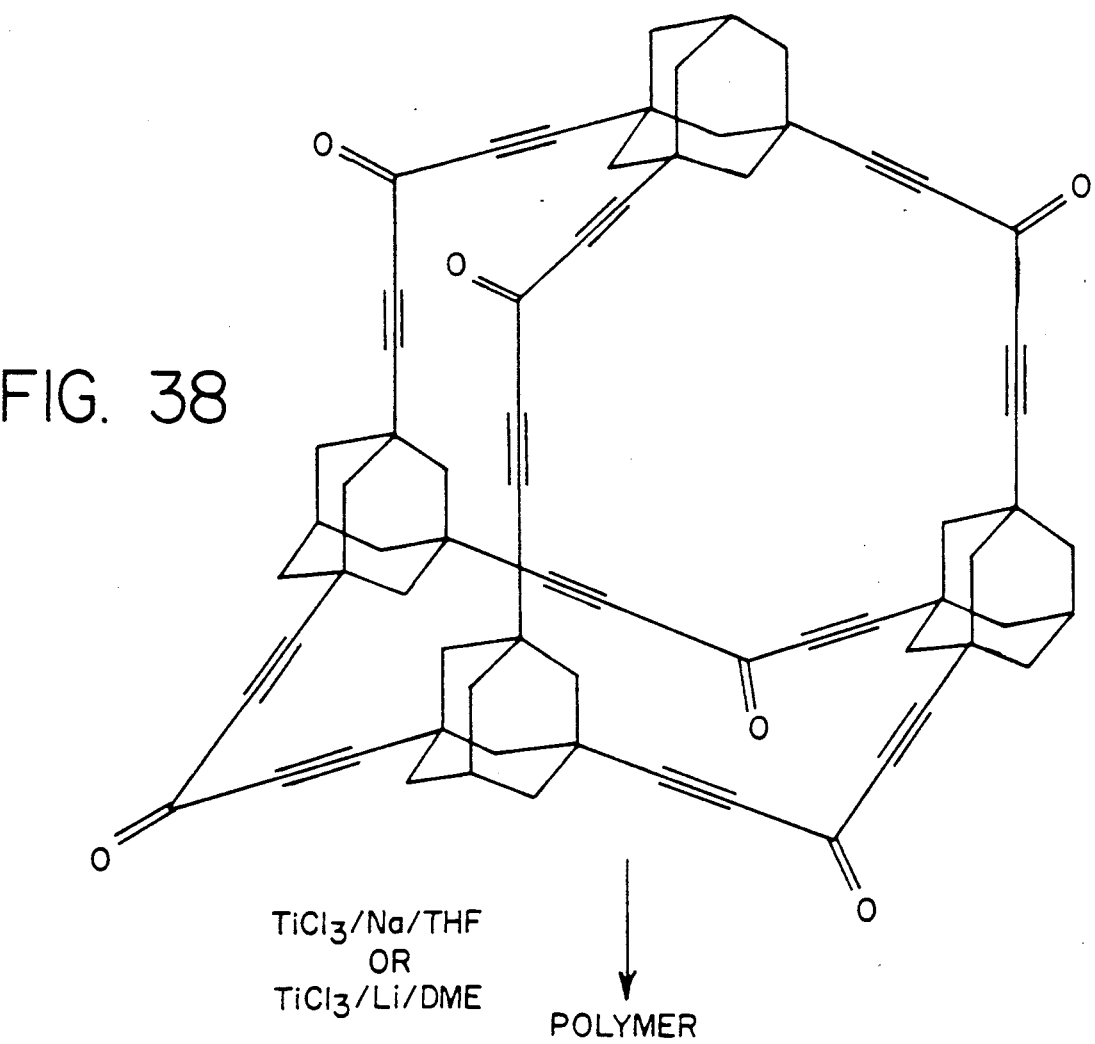
FIG. 38 shows one technique by which the monomer illustrated in FIG. 37 can be polymerized.

A nonlimiting example of X and Y replacement is shown by substitution of acetylene in the X position and adamantane in the Y position of an adamantane skeleton. One method by which this substitution may be achieved is the synthesis schematically shown in FIG. 37. The monomer may then be polymerized through McMurry coupling as shown in FIG. 38.

Z Replacement

Figure 39:
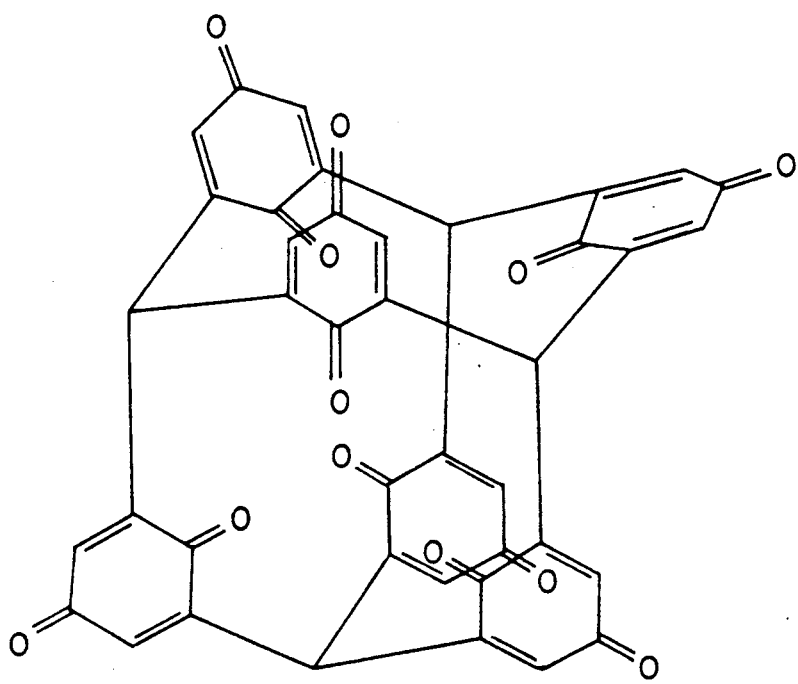
FIGS. 39, 40 and 41 show nonlimiting examples of methylene Z position substitutions in an adamantane skeleton.
Figure 40:
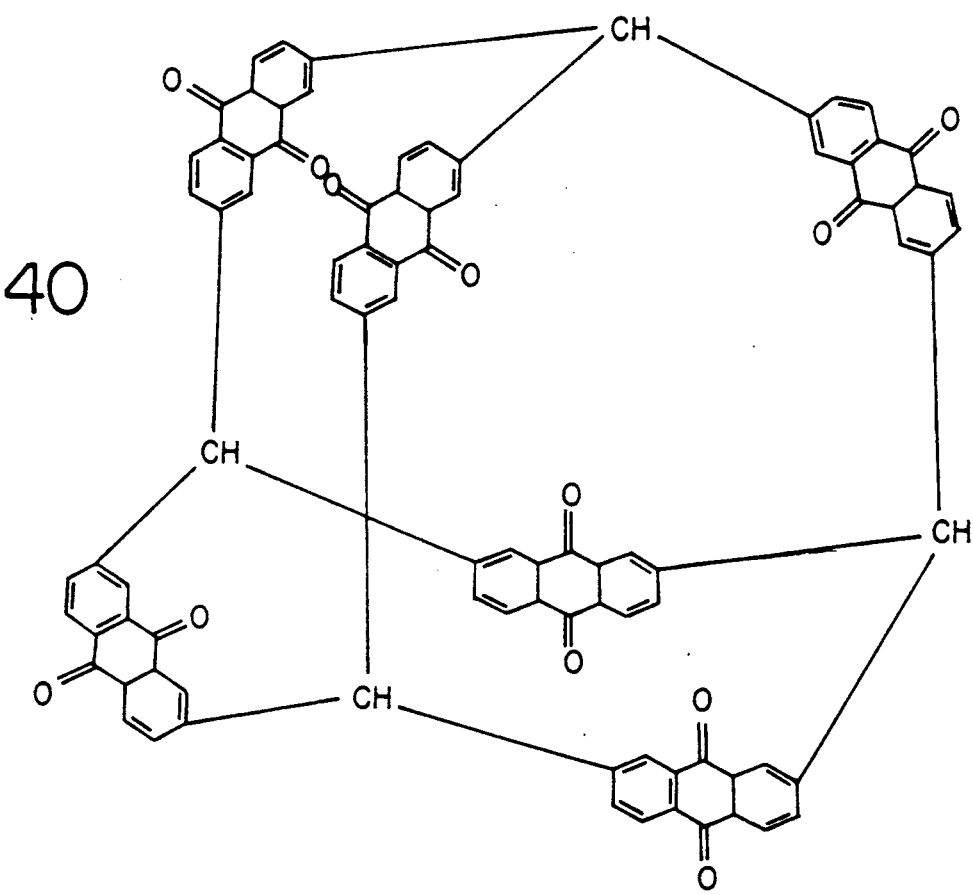
Figure 41:
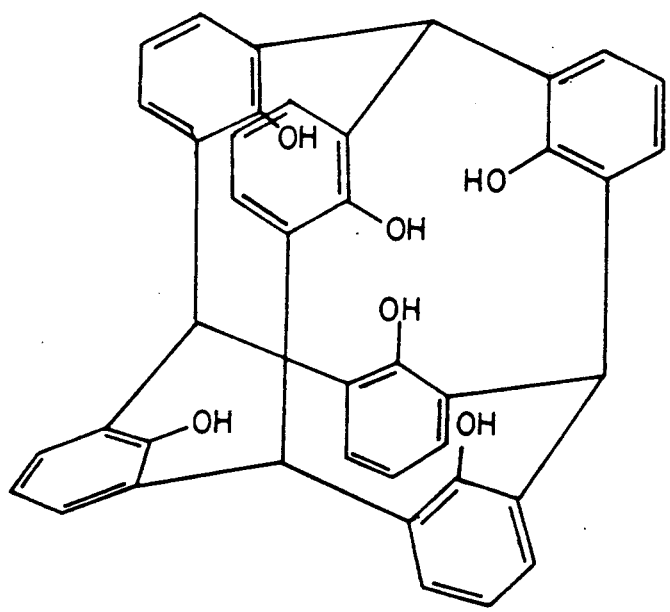

The structures illustrated in FIGS. 39, 40 and 41 show nonlimiting examples of methylene Z position substitutions in an adamantane skeleton. It is to be noted that the monomer of structure shown in FIG. 41 may be polymerized through single bonds linking octahedrally disposed benzene rings.

The substituted and/or expanded adamantane skeleton may be polymerized by linking two or more units as shown in FIGS. 39, 40 and 41 through the octahedrally disposed moieties. The adamantane skeleton units may bond directly to another monomer unit or may be spaced apart from the adjacent monomer units by the inclusion of substantially linear groups bonded to one or more moieties in the methylene Z positions. These spacing units are schematically illustrated as G in FIG. 42. X, Y, and Z have been deleted from FIG. 42 for clarity.

Nonlimiting examples of suitable G substituents are shown in FIG. 43, and are designated as 43a-43h, where n is at least 1, where Ad represents a unit having the skeletal structure of adamantane and where A, B, D and E are substituents including $C_6$-$C_{20}$ aromatics; linear, branched and cyclic $C_1$-$C_{20}$ alkyl groups; linear, branched and cyclic $C_2$-$C_{20}$ alkenyl groups, linear, branched and cyclic $C_2$-$C_{20}$ alkynyl groups; halogen; amines; diazo compounds; azide compounds; hydrazines, mercaptans; sulfides; polysulfides; ethers; alcohols; esters; organometallic compounds; amides; anhydrides; carbamates; ureas; imides; sulfonic acids; sulfinic acids; sulfinates; carboxylic acids; nitriles; isonitriles; heterocycles; metals; phosphates; phosphites; borates; ketones; aldehydes; aryl compounds; acid halides; hydrogen, and the reaction products thereof.

EXAMPLE XIV

A First Synthesis of the Linear Polymer From Adamantane 2,6-dione

In an argon glove bag, titanium trichloride (9.26 grams, 60 mmole) was weighed into an oven-dried three necked round-bottom flask equipped with a reflux condenser, an argon bubbler, and a magnetic stirrer. The flask was cooled with an ice-water bath, and 1,2-dimethyoxyethane (70 ml, distilled from LiAlH$_4$ and triphenylmethane) was added with stirring. A purple suspension resulted, and the cooling bath was removed. Lithium wire (3 mm, 1.249 gram, 180 mmole) was etched in methanol until it was shiny, then quickly cut into 2 mm segments, and added to the flask. The mixture as refluxed (oil bath) with stirring under argon for 5 hours, giving a black suspension. The oil bath was removed, and adamantane-2,6-dione (1.217 gram, 7.41 mmole) was added in one portion through the top of the condenser. This mixture was refluxed for 29 hours. The flask was then cooled, and the contents, including the unreacted lithium, were very carefully transferred into ice-cold 2N hydrochloric acid. The solid was collected on a sintered-glass funnel. The solid was then stirred in 2N hydrochloric acid overnight, filtered, washed with saturated aqueous Na$_2$EDTA, and washed with water. Drying gave the linear polymer as a gray solid (1.068 gram). The product was stable to 515° C. The product slowly decomposed above this temperature. At 550° C., decomposition occurred more rapidly, but no melting was observed. The density, determined by floatation in carbon tetrachloride-ethyl acetate, was 1.25 g/cm$^3$. The infrared spectrum (KBr) showed bands at 3439, 2951, 2909, 2844, 1446, 1350, 1323, 1306, 1203, 1084, 1037, 976, and 966 cm$^{-1}$. The solid-state CP-MAS $^{13}$CMR spectrum showed well-defined narrow signals at 133.4 (C=C), 74.0 (CHOH, end group), 41.7 (CH$_2$), and 32.5 (CH). Integration of the end group versus the other signals gave an average chain length of about 33 units. FAB mass spectrometry showed the highest fragment ion at m/z=2390 (>18 units). The linear polymer was not soluble in common organic solvents.

EXAMPLE XV

Synthesis of the Zig-Zag Polymer from Adamantane 2,4-dione

Titanium trichloride (1.85 g, 12.0 mmol) was weighed into an oven-dried 50-ml three-necked round-bottom flask in an argon glove-bag. The flask was fitted with a reflux condenser having an Ar bubbler and was cooled with an ice-water bath. After 20 ml of dry 1,4-dioxane was added to the flask with magnetic stirring and cooling, the cooling bath was removed. Sodium (0.828 g, 36.0 mmol) was added into the flask, and the mixture was refluxed for 0.75 hr with stirring to give a black suspension. After adding 0.657 g of (4.0 mmol) adamantane-2,4-dione from the top of the condenser in one portion, reflux was continued for 17.5 hours. The flask was cooled, and its contents were transferred to 160-ml 0.4N ice-cold aqueous HCl. Collection of the white solid floating on top of the aqueous layer gave 36 mg product (Fraction 1). The rest of the aqueous mixture was filtered on a sintered-glass funnel to collect 0.533 g of a grey solid (Fraction 2) after drying. The filtrate was extracted with 150 ml of hexanes; removal of the hexanes from the extract gave 62 mg of a solid (Fraction 3). Fractions 1 and 3 contained mostly adamantylideneadamantane, plus compounds judged to be longer oligomers by inspection of their NMR spectra. Fraction 2 was mostly polymer, and was characterized by its solid-state CP-MAS$^{13}$C-NMR: 133.3, 75.1 (small), 39.9, 37.1, 32.5, 29.1 (total olefinic/aliphatic integration: 1.0:6). FAB-MS: the highest m/e at 2596 (20 adamantane monomer units). All three fractions were combined and their flash chromatography on 40 g of silica gel gave the following fractions:

| Fraction | Eluent and amount (ml) | TLC R$_f$ value (solvent) | Residue |
|---|---|---|---|
| A | hexane (0–50) | 0.7 & 0.1 (CCl$_4$) | 164 mg semi-solid |
| B | hexanes (50–250) | 0.1 (CCl$_4$) | 11 mg semi-solid |
| C | CCl$_4$ (0–150) | 0.35 ≈ 0.9 (CCl$_4$) | 80 mg solid |
| D | CCl$_4$ (150–250) | 0.35 (CCl$_4$) | 20 mg solid |
| E | CHCl$_3$ (0–100) | 0.1 ≈ 0.6 (CHCl$_3$) | 125 mg solid |

| Fraction | Eluent and amount (ml) | TLC R_f value (solvent) | Residue |
|---|---|---|---|
| F | CHCl₃ (100–450) | ≈ 0.1 (CHCl₃) | 108 mg solid |

Fraction A: $^1$H- and $^{13}$C{$^1$H}-NMR (200 MHz, CDCl$_3$): adamantylidene-adamantane plus unknowns with some sharp and other broad lines in both spectra. It was composed of hydrocarbons because no alcohol carbon signals were observed in the $^{13}$C-NMR. Sublimation of Fraction A at 3 mm-Hg/100° C. gave 46 mg of oily crystals (Fraction A-1), which were predominantly the adamantane dimer by $^1$H-NMR spectrum. The residue was a waxy solid weighing 102 mg (Fraction A-2). FAB MX (Xe, NOBA) of Fraction A-2 show the highest m/e signal at 3058, corresponding to a chain length of 23 or more.

Fraction B: $^1$H-NMR (CDCl$_3$) unknown(s) with very broad lines. FAB MX shows the highest me/ signal at 3085, corresponding to a chain length of 23.

Fraction C: $^1$H-NMR and $^{13}$C{$^1$H}NMR (CDCl$_3$) polymeric alcohol(s) with broad lines in both spectra. FAB-MS: the highest m/e signal at 3099, corresponding to a chain length of 23.

Fraction D: $^1$H-NMR (CDCl$_3$) very broad lines indicating polymeric material. FAB-MS: the highest m/e signal at 3093, corresponding to a chain length of 23.

Fraction E: Part of the sample gave sharp lines in $^{13}$C-NMR with significant signals at 218.42, 135.88, 130.97, ≈96, 74.84, 46.96, 39.25, 36.31, 32.42 and 27.46 ppm, indicating the presence of both ketone and alcohol functional groups. The rest of the sample shows broad signals in olefinic, alcoholic, and aliphatic regions in $^{13}$C spectrum. The $^1$H-NMR spectrum was not informative. FAB-MS: the highest m/e signal at 3084, corresponding to a chain length of 23 or more.

Fraction F: Part of the sample gave sharp lines in $^{13}$C{$^1$H}-NMR with significant signals at 132.28, 96.12, 74.50, 67.07, 46.92, 40.90, 37.60, 36.52, 34.54, 31.02, 27.54 and 27.08, indicating the presence of alcohol. The rest of the sample shows broad signals in olefinic, alcoholic, and aliphatic regions. The $^1$H-NMR spectrum was again not very informative. FAB-MS: the highest m/e signal at 3098, corresponding to a chain length of 23.

EXAMPLE XVI

A First Synthesis of the Linear Oligomer

In a procedure similar to that used for preparation of the linear polymer of adamantane-2,6-dione, titanium chloride (3.857 grams, 25 mmole), 35 ml (dry) of 1,4-dioxane, and lithium wire (1.552 grams, 67.5 mmole, methanol-etched) were relxued for 1.75 hours. Adamantane-2,6-dione (0.082 grams, 0.5 mmole) and adamantanone (3.004 grams, 20 mmole) were added and the mixture was refluxed for 19 hours. After cooling, hexanes (35 ml) were added, and the mixture was filtered through a Florisil pad. After washing with hexanes, removal of the solvent gave the linear oligomers as a colorless solid (2.702 grams). Careful flash chromatography of the crude product on silica gel using hexanes eluted first a mixture of dimer and linear trimer and then a fraction (11 mg) containing linear trimer and tetramer. Washing the latter fraction with chloroform gave the linear tetramer (4 mg, m.p. >360° C.). The linear tetramer showed the expected parent ion z/e=532.4037 (calculated 532.4069) in the high-resolution mass spectrum. The low-resolution mass spectrum (70 eV) showed peaks at m/z of 534.47, 533.47, 532.46 (base peak), 469, 266.75, [(M=1)/2e], 266.24 (M/2e). The 500 MHz HMR spectrum (CHCl$_3$) showed broad, overlapping singlets (12H) at 3.01, 2.98, and 2.94 ppm and peaks at 1.94 (broad singlet, 4H), 1.86 (doublet, 11.9 Hz, 8H), 1.84 (broad singlet, 4H), 1.79 (broad, singlet, 16H), and 1.70 (doublet, 11.9 Hz, 8H) ppm.

Sublimation of the dimer-trimer fraction at 5 mmHg and 105° C. gave pure dimer (2.461 grams), identified by GC/MS comparison and left linear trimer (0.136 grams). The linear trimer begins to sublime above 300° C. and melts at 347°–351° C. The linear trimer showed the expected parent ion at m/z=400.3134 (calculated: 400.3130) in the high resolution mass spectrum. The low-resolution mass spectrum showed peaks at m/e =402, 401, 400 (base peak), 279, 265, 213, 212, 211, 200, 155, 145, 143, 135, and 129. The infrared spectrum (KBr) showed peaks at 2946, 2907, 2845, 1447, 1204, 1087, 1060, 1035, 981, 969, 945, and 692 cm$^{-1}$. The 500 MHz $^1$HMR spectrum (CHCl$_3$) showed peaks at 2.94 (broad singlet, 8H), 1.94 (broad singlet, 4H), 1.86 (doublet, 11.7 Hz), and 1.83 ppm total 12H), 1.77 (broad singlet, 8H), and 1.70 (doublet, 11.7 Hz, 8H). The $^{13}$C{$^1$H}-NMR/DEPT spectrum (CDCl$_3$) showed peaks at 133.45 (olefinic carbon), 132.80 (olefinic carbon), 41.55 (CH$_2$), 39.66 (CH$_2$), 37.88 (CH$_2$), 32.14 (CH), 31.96 (CH), and 28.60 (CH).

EXAMPLE XVII

A Second Synthesis of the Linear Oligomer

In a very similar procedure as described above in Example XV for the dimerization of adamantanone, titanium trichloride (3.857 g, 25.0 mmol) was refluxed with 1.552 g (67.5 mmol) sodium in 35 ml dry 1,4-dioxane for 1.75 hours. A mixture of 0.082 g (0.50 mmol) adamantane-2,6-dione and 3.004 g (20.0 mmol) adamantanone was added in one portion from the top of the condenser. The mixture was refluxed for another 19 hrs. Hexanes (35 ml) were added to the flask after cooling and the black mixture was filtered through a pad of Florisil. The Florisil was washed with hexanes. Removal of the solvents from the filtrate gave 2.702 g colorless solid. Careful flash chromatography of the crude product on 100 g of silica gel with hexanes eluted a mixture of the adamantane dimer and the linear trimer first, and later a fraction of 11 mg of a solid, which was a mixture of the linear adamantane trimer and the linear adamantane tetramer. Washing the latter with chloroform gave 4 mg of a solid (0.0075 mmol), which was shown to be the linear adamantane tetramer: M.p. >360° C. $^1$H-NMR (CDCl$_3$,500 MH$_2$)δ3.01, 2.98, 2.94 (overlapping br s, 12H total), 1.94 (br s, 4H), 1.86 (d, 11.9 Hz, 8H), 1.84 (br s, 4H), 1.79 (br s, 16H), 1.70 (d, 11.9 Hz, 8H). FT-IR (KBr, cm$^{-1}$) 2951 (m), 2907(s), 2845(s), 1446(m), 1350, 1328, 1308, 1203 (all w), 1086 (m), 1061, 1036, 981, 969 (all w). LRMS (70 ev): m/e 534.47, 533.47, 532.46 (base peak), 469, 266.75 [(M+1)/2e], 266.24 [M/2e]. HRMS calculated for C$_{40}$H$_{52}$: 532.4069, found: 532.4037. Sublimation of the dimer/trimer mixture at 5 mm-Hg/105° C. gave 2.461 g (9.169 mmol) dimer shown to be pure by GC/MS and leaving 0.136 g linear adamantane trimer (0.339 mmol) behind. The linear adamantane trimer was characterized by: m.p. 347°–51° C. (sublimed partially >300° C.). $^1$H-NMR (CDCl$_3$, 500 MHz): 2.94 (br s, 8H), 1.94 (br s, 4H), 1.86 (d, 11.65 Hz), and 1.83 (br s) these two signals represent 12 protons, 1.77 (br s, 8H), 1.70 (br d, 11.65 Hz, 8H). $^{13}C\{^1H\}$ and DEPT (CDCL$_3$, 90 MHz): 133.45, 132,80 (both s, C=C), 41.55 (CH$_2$), 39.66 (CH$_2$), 37.38 (CH$_2$), 32.14 (CH), 31.96 (CH), 28.60 (CH). HRMS calculated for C$_{30}$H$_{40}$: 400.3130, found 400.3134. LRMS 70 eV (m/e): 402, 401, 400 (base peak), 279, 265, 213, 212, 211, 200, 155, 145, 143, 135, 129. FT-IR (KBr, cm$^{-1}$): 2946(w), 2907(s), 2845(m), 1447, 1204, 1087, 1060, 1035, 981, 969, 945, 692 (all W). UV in hexanes: a tail absorption up to 235 nm.

EXAMPLE XVIII

A First Synthesis of the Nonlinear Trimer

The experimental procedure was identical to that used to prepare the linear dimer and tetramer except that the adamantane-2,4-dione (0.082 gram, 0.50 mmole) was used in place of adamantane-2,6-dione and the final reflux was for 15 hours. The crude product was a white solid (2.694 grams). Sublimation (5 mmHg, 105° C.) gave adamantylidieneadamantone (2.495 grams) and left the non-linear trimer (0.061 grams). The non-linear trimer (m.p. 258°-260° C.) showed the expected HR-MS parent ion at m/z=400.3135 (calculated: 400.3130). The low resolution mass spectrum (70 eV) showed peaks at z/e=402, 401, 400 (base peak), 359, 321, 265, 251, 212, 211, 200, 167, 155, 145, 144, 143, 142, 141, 135, and 129. The infrared spectrum KBr) showed peaks at 3010, 2949, 2906, 2845, 1447, 1350, 1339, 1327, 1260, 1215, 1193, 1181, 1101, 1085, 1072, 1063, 1042, 1008, 996, 971, 959, 943, 929, 809, 801, 790, 762, 706, 683, and 557 cm$^{-1}$. The ultraviolet spectrum in hexanes showed $\lambda_{max}(\epsilon)$ at 227 (2850), 224 (5130), and 221 nm (7600). The 500 Mhz $^1$HMR spectrum (CDCl$_3$) showed peaks at 3.90 (broad singlet, 1H), 2.93 (broad singlet, 4H), 2.86 (broad singlet, 2H), and 1.92–1.56 (multiplet, ca. 33H) ppm. The $^{13}C\{^1H\}$-NMR/DEPT spectrum (CDCl$_3$) showed peaks at 133.65 (olefinic carbon), 132.47 (olefinic carbon), 41.97 (CH$_2$), 39.74 (CH$_2$), 39.40 (CH$_2$), 39.22 (CH$_2$), 39.20 (CH$_2$), 37.36 (CH$_2$), 39.95 (CH), 28.81 (CH), 28.60 (CH), and 28.52 (CH), ppm.

EXAMPLE XIX

Synthesis of the Expanded Adamantane Skeleton

Synthesis of the monomer is carried out by adding 3 parts of phosgene or bis-imidazole carbonyl to 2 parts of 3-ethynyl-1,4-pentadiyne in a suitable solvent such as tetrahydrofuran. The polymer formed is removed and the two isomeric products are separated via chromatography on silica gel and is recognized by its characteristic NMR spectrum.

EXAMPLE XX

Synthesis of the Zig-Zag Polymer from Adamantane-2,4-dione

Inside an argon glove-bag, TiCl$_3$ (1.85 g, 12.0 mmol) in an oven-dried flask equipped with a reflux condenser and an argon bubbler was cooled with an ice-water bath and 1,4-dioxane (20 mL, distilled from sodium) was added with magnetic stirring and cooling. A purple suspension resulted, and the cooling bath was removed. Sodium (0.828 g, 36 mmol) was added, and the mixture was refluxed under argon for three quarters of an hour giving a black suspension. The oil bath was removed and adamantane-2,4-dione (0.657 g. 4,0 mmol) was added from the top of the condenser in one portion. The mixture was then refluxed for 17.5 hours. After cooling, the contents of the flask were transferred to ice-cold HCl (160 mL of 0.4N). Collection of the white solid floating on the aqueous layer gave 36 mg of solid (Fraction 1); filtration with a sintered-glass funnel gave 0.533 mg of a grey solid (Fraction 2) after drying; extraction of the filtrate with hexanes (150 mL) gave 62 mg of another solid (Fraction 3). NMR analysis of Fractions 1 and 3 showed that they were primarily adamantylideneadamantane and oligomers. Fraction 2 was very soluble in CCl$_4$, CHCl$_3$, CH$_2$Cl$_2$ and hot dioxane and partially soluble in hexanes, ethyl acetate, and acetone. Solid-state CP-MAS $^{13}$CMR showed peaks at 133.3, 75.1, 39.9, 37.1, 32.5 and 29.1 ppm, and FAB mass spectrometry showed the highest m/z at 2596 indicating a chain length of at least 20 units. All three fractions were combined and flash chromatographed on silica gel giving Fractions A–F.

| Fraction | Eluent | TLC Rf (solvent) | Dry Weight |
|---|---|---|---|
| A | hexanes | 0.7, 0.1 (CCl$_4$) | 164 mg |
| B | hexanes | 0.1 (CCl$_4$) | 11 mg |
| C | CCl$_4$ | 0.35–0.9 (CCl$_4$) | 80 mg |
| D | CHCl$_4$ | 0.35 (CHCl$_4$) | 20 mg |
| E | CHCl$_3$ | 0.1–0.6 (CHCl$_3$) | 125 mg |
| F | CHCl$_3$ | 0.1 (CHCl$_3$) | 108 mg |

Fraction A consisted of adamantylidene-adamantane and an unknown by proton and carbon NMR analysis. Sublimation (3 mm-Hg at 100° C.) gave adamantylidene-adamantane; the residue was a waxy solid (102 mg). The FAB mass spectrum of this solid showed the highest m/z at 3058 indicating a chain length of at least 23 units.

Fraction B showed very broad lines in the proton NMR, and the FAB mass spectrum showed the highest m/z at 3085 corresponding to a chain length of at least 23 units.

Fraction C showed broad lines in the proton and carbon NMR spectra; in addition signals due to COH groups were visible. The FAB mass spectrum showed the highest m/z at 3099 indicating a chain of at least 23 units.

Fraction D gave a proton NMR spectrum with very broad lines; the FAB mass spectrum showed the highest m/z at 3093 consistent with a chain of at least 23 units.

Fraction E showed sharp signals in the carbon NMR specrum at 218.42, 135.88, 130.97, 96, 74.84, 46.96, 39.25, 36.31, 32.42 and 27.46 ppm indicating the presence of both alcohols and ketones; the rest of the spectrum shows broad signals in the olefinic, alcoholic and aliphatic regions. The FAB mass spectrum shows the highest m/z at 3084 consistent with a chain of at least 23 units.

Fraction F showed sharp lines in the carbon NMR spectrum at 132.28, 96.12, 74.50, 67.07, 46.92, 40.90, 37.60, 36.52, 34.54, 31.02, 27.54 and 27.08 indicating the presence of COH; the rest of the spectrum showed broad signals in the olefinic, alcoholic and aliphatic regions. The FAB mass spectrum showed the highest m/z at 3098 consistent with a chain of at least 23 units.

EXAMPLE XXI

Synthesis of Adamantane Dimer Dichlorides

Adamantane dimer (5.369 g, 20.0 mmol) having the structure 44a shown in FIG. 44, was dissolved in 150 ml dry CH$_2$Cl$_2$ and 5.742 g (43.0 mmol) powdered NCS added in one portion. The mixture was stirred at room temperature for 10 hours, transferred to a separatory funnel, and diluted with $CH_2Cl_2$ to 200 ml. It was washed with 5×100 ml water and 100 ml saturated brine, and dried with anhydrous $Na_2SO_4$. Removal of solvent gave 6.887 g white solid. The GC/MS of this mixture showed five peaks with total ion integration about 2:10:9:55:25. The first peak was the monochloride of the adamantane dimer, shown as 44b in FIG. 44. The next two peaks belong to the structures designated as 45a and 45b in FIG. 45. The last two peaks represented four dichlorides having structures schematically shown as 45c, 45d, 45e and 45f in FIG. 45. A sample prepared similarly shows the following NMR spectra: $^1H$ NMR ($CDCl_3$, 360 MHz): δ4.25-4.09 (several br s, the major one at 2.21 ppm, 2H), 3.03 (br s, 2H), 2.86 (br s, 2H), 2.57-2.38 (m, 2H), 2.35-2.31 (m, 2H), 2.13 (br s, 2H), 2.05-1.99 (m, 2H), 1.92-1.83 (m, 4H), 1.69-1.62 (m, 6H), 1.51-1.45 (m, 2H). $^{13}C\{^1H\}$ and DEPT ($CDCl_3$, 90 MHz): δ141.69, 141.01, 128.55, 127.23 (C=C for structures 45a and 45b), 134.70, 134.68 (C=C for structures 45c-45f), 67.91, 67.82, 67.78, 67.70, 67.15, 64.31 (CHCl for structures 46a-46f).

EXAMPLE XXII

Synthesis of Adamantane Dimer Diketones

Ninety-five percent of the dichloride mixture obtained above in Example XXI (19.0 mmol) was treated with 5.707 g (57.0 mmol) $KHCO_3$ in 150 ml dry DMSO at 150° C. for 5 days with magnetic stir under Ar, at the end of which the GC/MS of the reaction mixture showed very little chloroketone intermediates. The mixture was poured into a ≈400 g crushed ice, neutralized to pH≈7 with aqueous HCl and filtered to collect some yellow solid. Extracting the aqueous layer with 5×80 ml ether, washing the combined ether solution with 6×100 ml water and 100 ml saturated brine, drying the organic layer with anhydrous $NaSO_4$, and removing the organic solvents gave 0.51 g of yellow solid. Both crops of crude product contained some hydroxyketones; therefore, they were combined, dissolved in 150 ml of dry $CH_2Cl_2$, and 1.0 g powdered PCC (Aldrich) was added. The mixture was stirred at room temperature for 5 hours. Another 0.50 g PCC was added and stirring continued for 2 more hours. Usual work-up gave 5.44 g of brown solid. Filtering this through 15 g silica gel with EtOAc/hexanes gave 5.32 g yellow solid as crude product. Flash chromatography on 125 g silica gel eluting with a gradient of hexanes to 1:3 (v/v) EtOAc/hexanes gave 0.045 g of adamantane dimer diketones having the structure 46e and 0.736 g of adamantane dimer diketones having the structures of 46d (13%) together with 3.34 g of other dione fractions containing structures 46a-g, all of which are shown in FIG. 46. Total dione yield was 73%. A small amount of dione 46b can be purified by repeated recrystallization in 1:3 (v/v) EtOAc/hexanes of one fraction obtained similarly during a small scale run. The NMR data for 46f was extracted from a mixture of 46f, 46e and 46b in about 47:40:13 ratio. Similarly, NMR data for 46b and 46c were extracted from two mixtures containing 46f, 46b, 46a and 46c in molar ratio of about 9:29:43:19 and 3:14:59:24. Structure 46a: $^1H$ NMR ($CDCl_3$, 360 MHz): δ3.56 (br s, 2H), 3.06 (br s, 2H), 2.59 (br s, 2H), 2.20-1.75 (m, 18H). $^{13}C\{^1H\}$ and DEPT ($CDCl_3$, 90 MHz):δ 215.01 (C=O), 134.17 (C=C), 52.83 (CH), 46.25 (CH), 41.91 ($CH_2$), 38.84 ($CH_2$), 38.02 ($CH_2$) 37.83 ($CH_2$), 31.08 (CH), 27.59 (CH). Structure 47b: $^1H$ NMR ($CDCl_3$, 360 MHz):δ3.56 (br s, 2H), 3.06 (br s, 2H), 2.63 (br s, 2H), 2.16-2.05 (m, 10H), 2.01-1.94 (m, 4H), 1.87-1.82 (m, containing a d with J=12.45 Hz, 2H), 1.81-1.76 (m, containing a d with J=12.45 Hz, 2H). $^{13}C\{^1H\}$ and DEPT ($CDCl_3$, 90 MHz): δ215.38 (C=O), 134.24 (C=C), 52.95 (CH), 46.38 (CH), 41.90 ($CH_2$), 38.88 ($CH_2$), 38.30 ($CH_2$), 37.70 ($CH_2$), 31.14 (CH), 27.54 (CH). Structure 46c: $^1H$ NMR ($CDCl_3$, 360 MHz): δ3.56 (br s, 2H), 3.06 (br s, 2H), 2.63 (br s, 2H), 2.20-1.75 (m, 18H). $^{13}C\{^1H\}$ and DEPT ($CDCl_3$, 90 MHz): δ215.15 (C=O), 134.20 (C=C), 52.04 (CH), 46.29 (CH), 41.59 ($CH_2$), 38.84 ($CH_2$), 38.19 ($CH_2$), 38.02 ($CH_2$), 32.09 (CH), 27.51 (CH). Structure 46d: m.p. 200°-201° C. $^1H$ NMR ($CDCl_3$, 360 MHz): δ3.57 (br s, 2H), 3.06 (br s, 2H), 2.59 (br s, 2H), 2.16-1.88 (m, 14H), 1.90 (br d, J=12.46 Hz, 2H), 1.75 (br d, J=12.62 Hz, 2H). $^{13}C\{^1H\}$ and DEPT ($CDCl_3$, 90 MHz): δ214.26 (C=O), 134.03 (C=C), 51.84 (CH), 46.20 (CH), 42.38 ($CH_2$), 38.99 ($CH_2$), 38.36 ($CH_2$), 37.62 ($CH_2$), 32.05 (CH), 27.73 (CH). FT-IR (KBr, $cm^{-1}$) 2922, 2855, 1713, 1687 (all s), 1639 (m), 1440 (m), 1345, 1312, 1277 1232, 1219, 1165, 1112, 1105, 1085 (all w), 1066 (m), 1043, 1029, 1020, 1003, 995, 973, 965, 935, 927, 908, 897, 881, 875, 868, 844, 788, 538, 502 (all w). UV ($1.15 \times 10^{-4}$ M in EtOH) $_{max}(\epsilon)$: 233 (7.48×$10^3$), 299 ($1.05 \times 10^3$). LRMS (70 eV, 100° C.) m/e (assignment, % of base peak): 298/297/296 (M+ cluster, 0.5/19.7/100), 269/268 (M-CO, 0.2/5.6), 241/240 (5/29), 199 (5), 197 (5), 155(4), 143(6), 141 (4), 129(10), 128 (9), 119(5), 118(3), 117(12), 115(11), 105(10), 103(4), 93( 92(6), 91(36). HRMS cacld for $C_{20}H_{24}O_2$ 296.1776, found 296.1774. 46e: $^1H$ NMR ($CDCl_3$, 360 MHz): δ3.79 (br d, J=1.57 Hz, 2H), 3.39 (br t, J=1.57 Hz, 1H), 2.92 (br s, 2H), 2.50-2.47 (m, 2H), 2.29 (br d, J=11.75 Hz, 2H), 2.23-2.19 (m, 1H), 2.15 (br d, J=11.75 Hz, 2H), 1.95-1.81 (m, 8H), 1.69 (br d, J=11.61 Hz, 2H), 1.60 (br d, J=12.50 Hz, 2H). $^{13}C\{^1H\}$ and DEPT ($CDCl_3$, 90 MHz): δ206.39 (C=O), 146.25 (C=C), 117.39 (C=C), 66.79 (CH), 50.08 (CH), 43.95 (CH), 40.53 ($CH_2$), 39.58 ($CH_2$), 36.66 ($CH_2$), 33.58 (CH), 27.95 (CH), 27.76 (CH), 27.61 (CH). FT-IR (KBr, $cm^{-1}$) 2912 (s), 2850(m), 1729 (s), 1703 (s), 1467 (w), 1450 (m), 1384, 1336, 1306, 1251 (all w), 1235 (m), 1102 (w), 1072 (m), 1035, 1015, 960, 944, 876, 805, 701, 574, 532 (all w). 46f: $^1H$ NMR ($CDCl_3$, 360 MHz): δ3.72 (br s, 2H), 2.89 (br s, 2H), 2.74 (br s 2H), 2.33 (br s, 2H), 2.31-2.27 (m, 2H), 2.20-1.80 (m, 8H), 1.69 (br d, J=12.3 Hz, 2H), 1.60 (br d, J=11.1 Hz, 2H). $^{13}C\{^1H\}$ and DEPT ($CDCl_3$, 90 MHz): δ211.97 (C=O), 143.51 (C=C), 125.56 (C=C), 50.30 (CH), 45.09 (CH), 40.05 ($CH_2$), 39.54 ($CH_2$), 39.45, 39.10 ($CH_2$), 36.69 ($CH_2$), 33.13 ($CH_2$), 27.90 (CH).

Changes and modifications in the specifically described embodiments can be carried out without departing from the scope of the invention which is intended to be limited only by the scope of the appended claims.

What is claimed is:

1. A polymer comprising at least three monomers bonded through octahedrally disposed non-metallic atoms of the monomers.

2. The polymer of claim 1 wherein said octahedrally disposed atoms have a valence of 4.

3. The polymer of claim 2 wherein said octahedrally disposed atoms comprise carbon.

4. The polymer of claim 1 comprising a pendant substituent group.

5. The polymer of claim 4 wherein said pendant substituent group comprises a terminal group.

6. The polymer of claim 4 wherein said pendant substituent group comprises a connecting group.

7. The polymer of claim 4 wherein said substituent group is selected from the group consisting of $C_6$–$C_{20}$ aromatics, $C_1$–$C_{20}$ alkyl groups, $C_2$–$C_{20}$ alkenyl groups, $C_2$–$C_{20}$ alkynyl groups, halogens, amines, diazo compounds, azide compounds, hydrazines, mercaptans, sulfides, polysulfides, ethers, alcohols, esters, organometallic compounds, amides, anhydrides, carbamates, ureas, imides, sulfonic acids, sulfinic acids, sulfinates, carboxylic acids, nitriles, isonitriles, heterocycles, metals, phosphates, phosphites, borates, ketones, aldehydes, aryl compounds, acid halides, hydrogen, and the reaction products thereof.

8. A polymer comprising at least three monomers bonded through octahedrally disposed carbon atoms of the monomers.

9. The polymer of claim 8 comprising a pendant substituent group.

10. The polymer of claim 9 wherein said pendant substituent group comprises a terminal group.

11. The polymer of claim 9 wherein said pendant substituent group comprises a connecting group.

12. The polymer of claim 9 wherein said substituent group is selected from the group consisting of $C_6$–$C_{20}$ aromatics, $C_1$–$C_{20}$ alkyl groups, $C_2$–$C_{20}$ alkenyl groups, $C_2$–$C_{20}$ alkynyl groups, halogens, amines, diazo compounds, azide compounds, hydrazines, mercaptans, sulfides, polysulfides, ethers, alcohols, esters, organometallic compounds, amides, anhydrides, carbamates, ureas, imides, sulfonic acids, sulfinic acids, sulfinates, carboxylic acids, nitriles, isonitriles, heterocycles, metals, phosphates, phosphites, borates, ketones, aldehydes, aryl compounds, acid halides, hydrogen, and the reaction products thereof.

13. The polymer of claim 8 wherein said monomer units bond to form a linear molecular unit.

14. The polymer of claim 8 wherein said monomer units bond to form a laminar structure.

15. The polymer of claim 14 wherein said laminar structure comprises a sheet.

16. The polymer of claim 8 wherein said monomer units bond to form a three-dimensional framework structure.

17. The polymer of claim 8 wherein said monomer units bond to form a molecular sieve cage structure.

18. The polymer of claim 8 wherein said monomer units bond to form a helical structure.

19. The polymer of claim 8 wherein said monomer nits comprise an adamantane skeleton.

20. The polymer of claim 19 further comprising a pendant substituent group.

21. The polymer of claim 20 wherein said pendant substituent group comprises a terminal group.

22. The polymer of claim 20 wherein said pendant substituent group comprises a connecting group.

23. The polymer of claim 20 wherein said substituent group is selected from the group consisting of $C_6$–$C_{20}$ aromatics, $C_1$–$C_{20}$ alkyl groups, $C_2$–$C_{20}$ alkenyl groups, $C_2$–$C_{20}$ alkynyl groups, halogens, amines, diazo compounds, azide compounds, hydrazines, mercaptans, sulfides, polysulfides, ethers, alcohols, esters, organometallic compounds, amides, anhydrides, carbamates, ureas, imides, sulfonic acids, sulfinic acids, sulfinates, carboxylic acids, nitriles, isonitriles, heterocycles, metals, phosphates, phosphites, borates, ketones, aldehydes, aryl compounds, acid halides, hydrogen, and the reaction products thereof.

24. The polymer of claim 19 wherein said monomer units bond to form a linear molecular unit.

25. The polymer of claim 19 wherein said monomer units bond to form a laminar structure.

26. The polymer of claim 19 wherein said laminar structure comprises a sheet.

27. The polymer of claim 19 wherein said monomer units bond to form a three-dimensional framework structure.

28. The polymer of claim 19 wherein said monomer units bond to form a molecular sieve cage structure.

29. The polymer of claim 19 wherein said monomer units bond to form a helical structure.

30. The polymer of claim 19 wherein said monomer units bond to form a laminar structure.

31. The polymer of claim 30 wherein said laminar structure comprises a sheet.

32. The polymer of claim 19 wherein said monomer units bond to form a three-dimensional framework structure.

33. The polymer of claim 19 wherein said monomer units bond to form a molecular sieve cage structure.

34. A polymer comprising at least three monomers bonded through octahedrally disposed non-metallic atoms of the monomers, wherein said octahedrally disposed atoms have a valence of 4, and wherein said polymer has the structure of the linear rod compound designated as 3c in FIG. 3, where n is at least 1.

35. A polymer comprising at least three monomers bonded through octahedrally disposed non-metallic atoms of the monomers, wherein said octahedrally disposed atoms have a valence of 4, and wherein said polymer has the structure of the compound designated as 7c in FIG. 7, wherein $X_1$ and $X_2$ have the skeletal structure of adamantane, and n is at least 1.

36. A polymer comprising at least 4 repeating units bonded through octahedrally disposed non-metallic atoms of the repeating units, wherein said octahedrally disposed atoms have a valence of 4, said repeating units having the structure of at least one selected from the group consisting of the compounds designated at 16a, 16b, 16c and 16d in FIG. 16.

37. A polymer comprising at least 5 repeating units bonded through octahedrally disposed non-metallic atoms of the repeating units, wherein said octahedrally disposed atoms have a valence of 4, said repeating units having the structure of at least one selected from the compounds designated as 17a and 17b in FIG. 17.

38. A polymer comprising at least 6 repeating units bonded through octahedrally disposed non-metallic atoms of the repeating units, wherein said octahedrally disposed atoms have a valence of 4, said repeating units having the structure of at least one selected from the compounds designated as 17c and 17d in FIG. 17.

39. A composition of matter having the structure of at least one selected from the group consisting of the compounds designated as 5a, 5b, 5c and 5d in FIG. 5, wherein Ad has the skeletal structure of adamantane, and repeating adamantane skeletal units are bonded together through octahedrally disposed nonmetallic atoms of the repeating adamantane units, and is at least 2, and wherein $R_1$ and $R_2$ each comprise one selected from the group consisting of hydrogen, and nonpolar constituent groups having from 1 to about 20 carbon atoms, and wherein $R_3$ and $R_4$ comprise constituent groups having from 1 to about 20 carbon atoms, with at least one of said $R_3$ and $R_4$ being polar.

40. The composition of claim 39 wherein at least one of the $R_3$ and $R_4$ comprises a carboxyl group.

41. The composition of claim 39 wherein $R_3$ and $R_4$ comprise carboxyl groups.

42. The composition of claim 41 wherein both $R_3$ and $R_4$ comprise COOH.

43. The polymer of claim 34 further comprising a terminal polar constituent selected from the group consisting of carboxylates, amines, quaternary ammonium salts, sulfonates and phosphates.

44. The polymer of claim 43 wherein said terminal polar constituent comprises a carboxyl group.

45. The polymer of claim 44 wherein said terminal polar constituent group comprises COOH.

46. The polymer of claim 43 further comprising a second terminal group which comprises an alkyl group having at least five carbon atoms.

47. A polymer comprising at least three monomers bonded through octahedrally disposed non-metallic atoms of the monomers wherein said octahedrally disposed atoms have a valence of 4 and wherein at least one octahedrally disposed carbon atom is bonded to an oxygen atom to form a ketone.

48. A method for converting compounds containing octahedrally disposed nonmetallic atoms to mono- and higher ketones of said compounds comprising the steps of:
   a) halogenating an octahedrally disposed nonmetallic moiety of said compound; and
   b) contacting said halogenated compound of step a) with base in the presence of DMSO (dimethyl sulfoxide) under conditions of elevated temperature for a period of time sufficient to convert at least a portion of said halogenated compound of step a) to the corresponding ketone.

49. The method of claim 48 further comprising repeating steps a) and b) to produce di-, tri-, or higher ketones.

50. The method of claim 49 further comprising linking at least one monoketone and at least one higher ketone by McMurry synthesis to form a polymer bonded through octahedrally disposed nonmetallic atoms of the monomers.

51. The method of claim 48 wherein said base is at least one selected from the group consisting of $KHCO_3$ and $NaHCO_3$.

* * * * *